US010865394B2

(12) United States Patent
Naegle et al.

(10) Patent No.: US 10,865,394 B2
(45) Date of Patent: Dec. 15, 2020

(54) TOOLKIT FOR THE PRODUCTION OF POST-TRANSLATIONALLY MODIFIED PROTEINS

(71) Applicants: Kristen Naegle, St. Louis, MO (US); Roman Sloutsky, St. Louis, MO (US)

(72) Inventors: Kristen Naegle, St. Louis, MO (US); Roman Sloutsky, St. Louis, MO (US)

(73) Assignee: Washington University, St. Louis, MO (US)

( * ) Notice: Subject to any disclaimer, the term of this patent is extended or adjusted under 35 U.S.C. 154(b) by 194 days.

(21) Appl. No.: 15/710,451

(22) Filed: Sep. 20, 2017

(65) Prior Publication Data

US 2018/0010102 A1    Jan. 11, 2018

Related U.S. Application Data

(63) Continuation-in-part of application No. PCT/US2016/044281, filed on Jul. 27, 2016.

(60) Provisional application No. 62/397,655, filed on Sep. 21, 2016, provisional application No. 62/197,385, filed on Jul. 27, 2015.

(51) Int. Cl.
| | |
|---|---|
| *C12N 9/12* | (2006.01) |
| *C12P 21/04* | (2006.01) |
| *C12N 15/00* | (2006.01) |
| *C07H 21/04* | (2006.01) |
| *C07K 14/00* | (2006.01) |
| *C12P 21/00* | (2006.01) |

(52) U.S. Cl.
CPC .............. *C12N 9/12* (2013.01); *C12P 21/00* (2013.01); *C07K 2319/00* (2013.01)

(58) Field of Classification Search
None
See application file for complete search history.

(56) References Cited

U.S. PATENT DOCUMENTS

| 6,184,205 | B1 * | 2/2001 | Sparks ................. | C07K 7/06 514/21.4 |
|---|---|---|---|---|
| 8,709,756 | B2 | 4/2014 | Cregg et al. | |
| 2003/0099932 | A1 | 5/2003 | Lorens et al. | |
| 2005/0125852 | A1 | 6/2005 | Caenepeel et al. | |
| 2012/0178647 | A1 * | 7/2012 | Joung ................. | C12N 15/1093 506/9 |
| 2015/0044712 | A1 | 2/2015 | Heo et al. | |

FOREIGN PATENT DOCUMENTS

| EP | 2810648 A1 | 12/2014 |
|---|---|---|
| WO | 2017019777 A1 | 2/2017 |

OTHER PUBLICATIONS

Terpe. Overview of tag protein fusions: from molecular and biochemical fundamentals to commercial systems. Appl Microbiol Biotechnol. Jan. 2003;60(5):523-33. Epub Nov. 7, 2002.*
Biondi, R. et al., "Identification of a pocket in the PDK1 kinase domain that interacts with PIF and the C-terminal residues of PKA," EMBO J., 2000, pp. 979-988, vol. 19, No. 5.
Couture, C.et al., "Regulation of the LckSH2 Domain by Tyrosine Phosphorylation," J. Biol. Chem., Oct. 4, 1996, pp. 24880-24884, vol. 271, No. 40.
International Search Report and Written Opinion dated Oct. 21, 2016 from related PCT Patent Application No. PCT/US2016/044281; 13 pgs.
Jin, L. et al., "Tyrosine Phosphorylation of the Lyn Src Homology 2 (SH2) Domain Modulates Its Binding Affinity and Specificity," Mol. Cell. Proteom., 2015, pp. 695-706, vol. 14, No. 3.
Mayer B. et al. "Signalling through SH2 and SH3 domains," Trends Cell Biol., Jan. 1993, pp. 8-13, vol. 3, No. 1, Elsevier Science Publishers Ltd (UK).
Mayer, B., "SH3 domains: complexity in moderation," J. Cell Sci., Apr. 2001, pp. 1253-1263, vol. 114, Pt. 7, The Company of Biologists Ltd.
Musacchio, A. et al., "SH3—an abundant protein domain in search of a function," FEBS, Jul. 1992, pp. 55-61, vol. 307, No. 1.
Pawson, T. et al., "SH2 and SH3 domains," Curr. Biol., Jul. 1, 1993, pp. 434-442, vol. 3, No. 7.
Pawson, T., "Protein modules and signalling networks," Nature, Feb. 16, 1995, pp. 573-580, vol. 373, No. 6515.
Pisabarro, M. et al., "Rational Design of Specific High-Affinity Peptide Ligands for the Abl-SH3 Domain," Biochem., Aug. 20, 1996, pp. 10634-10640, vol. 35, No. 33.
Pisabarro, M. et al., "Crystal Structure of the Abl-SH3 Domain Complexed with a Designed High-affinity Peptide Ligand: Implications for SH3-Ligand Interactions," J. Mol. Biol., Aug. 21, 1998, pp. 513-521, vol. 281, No. 3, Article mb981932.
Rettenmaier, T. et al., "A small-molecule mimic of a peptide docking motif inhibits the protein kinase PDK1," PNAS, Dec. 30, 2014, pp. 18590-18595, vol. 111, No. 52.
Rigaut, G. et al., "A generic protein purification method for protein complex characterization and proteome exploration," Nat Biotechnol., Oct. 1999, pp. 1030-1032, vol. 17, Nature America Inc.

(Continued)

*Primary Examiner* — Yong D Pak
(74) *Attorney, Agent, or Firm* — Polsinelli PC

(57) ABSTRACT

The present disclosure provides a system to produce soluble, folded, and post-translationally modified proteins. The system includes a fusion protein comprising a catalytic domain of an enzyme involved in post-translational protein modification and a targeting domain, and a substrate protein comprising a protein of interest and a sequence that interacts with the targeting domain. The present disclosure also provides polynucleotide sequences encoding fusion proteins and substrate proteins, vectors for expressing polynucleotide sequences, vectors comprising the polynucleotide sequences, and isolated cells comprising said vectors.

Figure 1:
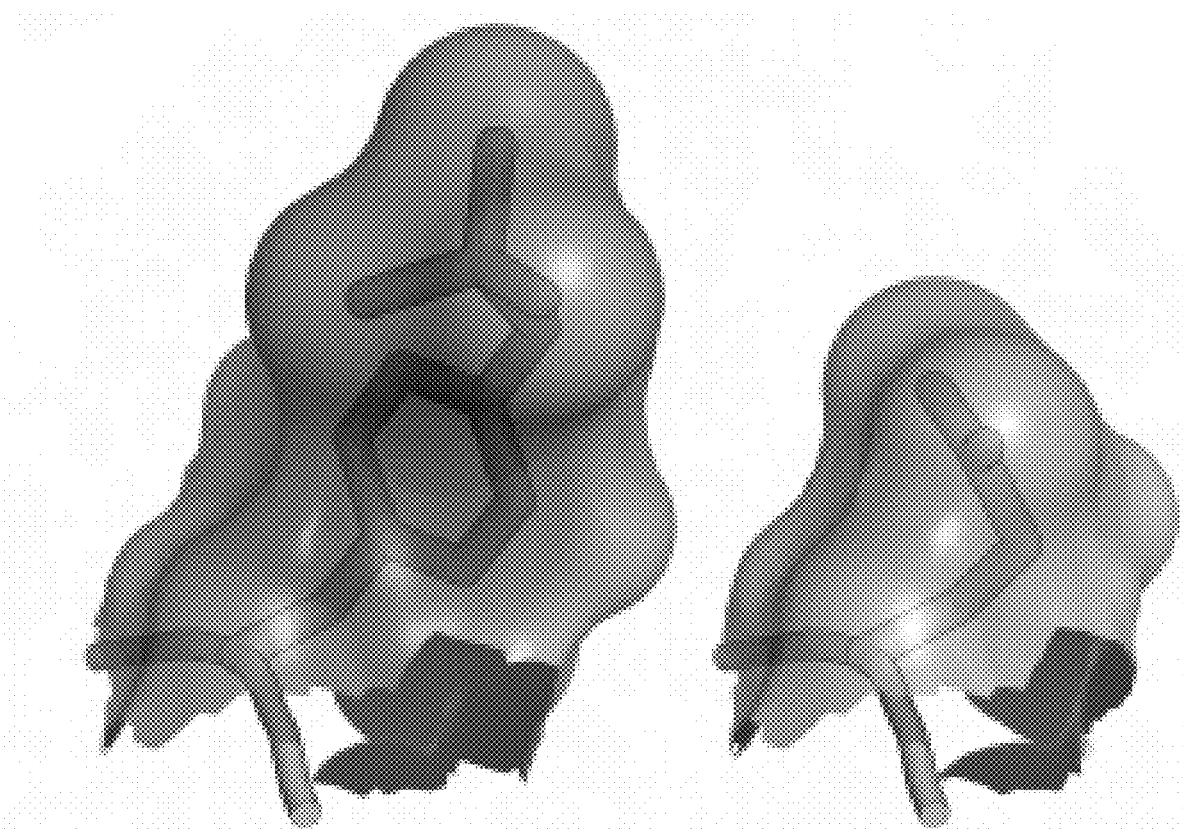

10 Claims, 6 Drawing Sheets
(6 of 6 Drawing Sheet(s) Filed in Color)
Specification includes a Sequence Listing.

(56) References Cited

OTHER PUBLICATIONS

Stover, D. et al., "Modulation of the SH2 Binding Specificity and Kinase Activity of Src by Tyrosine Phosphorylation within Its SH2 Domain," J. Biol. Chem., May 24, 1996, pp. 12481-12487, vol. 271, No. 21.

Weng, Z. et al., "Structure-Function Analysis of SH3 Domains: SH3 Binding Specificity Altered by Single Amino Acid Substitutions," Mol. Cell Biol., Oct. 1995, pp. 5627-5634, vol. 15, No. 10.

Whisstock J. et al., "SH3 domains in prokaryotes," Trends Biochem. Sci., Apr. 1999, pp. 132-133, vol. 24, No. 4, Elsevier Science.

Wu, D. et al., "Peptide reporters of kinase activity in whole cell lysates," NIH Public Access Author Manuscript, available in PMC Jan. 1, 2011, pp. 1-22, Published in final edited form as: Biopolymers, 2010, pp. 475-486, vol. 94, No. 4.

* cited by examiner

Red (680): anti-Myc
Green (800): anti-phosphotyrosine

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence

```
<220> FEATURE:
<223> OTHER INFORMATION: SYNTHESIZED
<220> FEATURE:
<221> NAME/KEY: misc_feature
<222> LOCATION: (2)..(3)
<223> OTHER INFORMATION: Xaa can be any naturally occurring amino acid

<400> SEQUENCE: 1

Pro Xaa Xaa Pro
1

<210> SEQ ID NO 2
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 2

Ala Pro Thr Met Pro Pro Pro Leu Pro Pro
1               5                   10

<210> SEQ ID NO 3
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 3

Ala Pro Thr Tyr Ser Pro Pro Pro Pro Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 4

Ala Pro Ser Tyr Ser Pro Pro Pro Pro Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: STNTHESIZED

<400> SEQUENCE: 5

Ser Leu Asp Asn Gly Gly Tyr Tyr Ile Ser Pro Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 6

Ser Leu Asp Asn Gly Gly Tyr Tyr Ile Ser Pro Arg
1               5                   10

<210> SEQ ID NO 7
```

```
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 7

Ser Leu Asp Asn Gly Gly Tyr Tyr Ile Ser Pro Arg Arg
1               5                   10
```

TOOLKIT FOR THE PRODUCTION OF POST-TRANSLATIONALLY MODIFIED PROTEINS

CROSS REFERENCE TO RELATED APPLICATIONS

This application claims the priority of U.S. provisional application No. 62/397,655, filed Sep. 21, 2016, and is also a continuation-in-part of PCT application number PCT/US2016/044281 filed Jul. 27, 2016, which claims the priority of U.S. provisional application No. 62/197,385, filed Jul. 27, 2015, each of which is hereby incorporated by reference in its entirety.

GOVERNMENTAL RIGHTS

This invention was made with government support under CA212726 awarded by the National Institutes of Health. The government has certain rights in the invention.

FIELD OF THE INVENTION

The present disclosure provides a system to produce soluble, folded, and post-translationally modified proteins. The system includes a fusion protein comprising a catalytic domain of an enzyme involved in post-translational protein modification and a targeting domain, and a substrate protein comprising a protein of interest and a sequence that interacts with the targeting domain. The present disclosure also provides polynucleotide sequences encoding fusion proteins and substrate proteins, vectors for expressing polynucleotide sequences, vectors comprising the polynucleotide sequences, and isolated cells comprising said vectors.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Advances in understanding the effects of post-translational modifications on protein function are hindered by the inability to efficiently and cost-effectively make specific forms of modified proteins. For example, the LYN SH2 domain is consistently phosphorylated in chronic lymphocytic leukemia and acute myeloid leukemia. ProteomeScout, a database of post-translational modification experiments, identifies a number of studies that capture quantitative measurements of SH2 domain phosphorylation. This data paints a picture of differential phosphorylation of a number of SH2 domain phosphorylation sites across human cancers, including dynamic changes in response to treatment with a BCR-ABL inhibitor, alterations in human glioblastoma xenografts, and in response to HER2 over-expression in a model cell system. Taken together, these studies suggest a connection between SH2 domain phosphorylation and a number of human cancers Several methods are used to study the effect of phosphorylation on a substrate protein. Two of these systems are tractable to the basic researcher and include: 1) in vitro phosphorylation of a recombinant protein with a recombinant kinase and 2) mutation of the target tyrosine in the substrate protein to a glutamic acid (i.e. phosphomimics). The first is used rarely as it requires either knowledge of the kinase responsible or significant effort in identifying a kinase. The second is easily implemented by simple molecular biology techniques. However, as demonstrated in FIG. 1, phosphomimics fail to recapitulate the size, shape and charge of a phosphorylated tyrosine. Two additional methods for producing phosphorylated proteins or phosphoprotein substitutes warrant mention, but are much less tractable to most systems and research labs. These include: 1) chemical ligation, i.e. the linkage of a synthesized phosphopeptide fragment with a recombinant protein and 2) the incorporation of a synthetic amino acid via a Staudinger reaction. Chemical ligation is limited by the fidelity of phosphopeptide synthesis, meaning that only tyrosines that are within about 20 to 45 amino acids of the N-terminus can possibly be studied by this method. FIG. 2 demonstrates that most tyrosines of interest fall outside of this range, even on a small protein such as an SH2 domain. And for synthetic amino acids, the best synthetic amino acid analog is not an exact match to phosphotyrosine, as a result of the azide group required for the reaction. Additionally, protein translation with synthetic amino acids is not a technique that the majority of research labs can incorporate readily.

Therefore, the most tractable approaches to studying tyrosine phosphorylation are still a significant barrier to the progress of basic research. Similar barriers exist for studying other forms of post-translational modification. Improved methods are needed in the art.

SUMMARY OF THE INVENTION

In an aspect, the present disclosure encompasses an isolated fusion protein, the fusion protein comprising a catalytic domain of enzyme involved in post-translational protein modification, a targeting domain and a linker, wherein the catalytic domain and the targeting domain are joined by the linker. The linker contains repeats of two, oppositely-charged, amino acids, and is about 10 to about 30 amino acids in length. The isolated fusion protein may further comprise 1, 2, 3, 4, 5, 6, 7, 8, 9 or more peptide tags at either the N-terminus or the C-terminus, each independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a polynucleotide sequence encoding the fusion protein of the preceding paragraph. The polynucleotide sequence may be operably linked to a regulated promoter or a constitutive promoter. In another aspect, the present disclosure encompasses a vector comprising the polynucleotide sequence encoding the fusion protein. In another aspect, the present disclosure encompasses a host cell comprising the vector.

In another aspect, the present disclosure encompasses an isolated fusion protein comprising a kinase catalytic domain, a targeting domain and a linker, wherein the kinase catalytic domain and the targeting domain are joined by the linker. In certain embodiments the kinase catalytic domain is constitutively active. The isolated fusion protein may further comprise 1, 2, 3, 4, 5, 6, 7, 8, 9 or more peptide tags at either the N-terminus or the C-terminus, each independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a polynucleotide sequence encoding the fusion protein of the preceding paragraph. The polynucleotide sequence may be operably linked to a regulated promoter or a constitutive promoter. In another aspect, the present disclosure encompasses a vector comprising the polynucleotide sequence encoding the fusion protein. In another aspect, the present disclosure encompasses a host cell comprising the vector.

In another aspect, the present disclosure encompasses a polynucleotide sequence encoding a substrate protein, the substrate protein comprising a polypeptide of interest, a sequence that interacts with a targeting domain, a protease cleavage site, and an optional linker. The sequence that interacts with the targeting domain is at least 4 amino acids in length. The protease cleavage site is between the polypeptide of interest and the linker when the linker is present, and between the polypeptide of interest and the sequence that interacts with the targeting domain when the linker is not present. The optional linker contains repeats of two, oppositely-charged, amino acids, and is about 10 to about 30 amino acids in length. The polynucleotide may further encode 1, 2, 3, 4, 5, 6, 7, 8, 9 or more peptide tags at either the N-terminus or the C-terminus of the substrate protein, each peptide tag independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a kit for producing a post-translationally modified protein of interest, the kit comprising a first vector and a second vector, wherein (a) the first vector comprises a polynucleotide sequence encoding a targeting domain, a linker, and a multiple cloning sequence, wherein the multiple cloning sequence is proximal to the linker and at the end of the linker opposite the targeting domain, and the polynucleotide sequence is operably linked to a promoter; and (b) second vector comprises a polynucleotide sequence encoding a sequence that interacts with a targeting domain, protease cleavage site, and a multiple cloning sequence, wherein the multiple cloning sequence is proximal to protease cleavage site and at the end of the protease cleavage site opposite the sequence that interacts with the targeting domain.

In another aspect, the present disclosure encompasses a kit for producing a phosphorylated protein of interest, the kit comprising a first vector and a second vector, wherein (a) the first vector comprises a polynucleotide sequence encoding a targeting domain, a linker, and a multiple cloning sequence, wherein the multiple cloning sequence is proximal to the linker and at the end of the linker opposite the targeting domain, and the polynucleotide sequence is operably linked to a promoter; and (b) the second vector comprises a polynucleotide sequence encoding a sequence that interacts with the targeting domain, protease cleavage site, and a multiple cloning sequence, wherein the multiple cloning sequence is proximal to protease cleavage site and at the end of the protease cleavage site opposite the sequence that interacts with the targeting domain.

In another aspect, the present disclosure encompasses a kit for producing a post-translationally modified protein of interest, the kit comprising a first vector and a second vector, wherein (a) the first vector comprises a polynucleotide sequence encoding a targeting domain, a linker, and a catalytic domain of an enzyme involved in posttranslational modification, wherein the catalytic domain and the targeting domain are joined by the linker, and the polynucleotide sequence is operably linked to a promoter; and (b) the second vector comprises a polynucleotide sequence encoding a sequence that interacts with the targeting domain, protease cleavage site, and a multiple cloning sequence, wherein the multiple cloning sequence is proximal to protease cleavage site and at the end of the protease cleavage site opposite the sequence that interacts with the targeting domain. In certain embodiments, the catalytic domain of an enzyme involved in posttranslational modification is a kinase catalytic domain or a constitutively active kinase catalytic domain.

In another aspect, the present disclosure encompasses an isolated fusion protein, the fusion protein comprising a catalytic domain of enzyme involved in post-translational protein modification, an SH3 domain and a linker, wherein the catalytic domain and the SH3 domain are joined by the linker. The linker contains repeats of two, oppositely-charged, amino acids, and is about 10 to about 30 amino acids in length. The isolated fusion protein may further comprise 1, 2, 3, 4, 5, 6, 7, 8, 9 or more peptide tags at either the N-terminus or the C-terminus, each independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a polynucleotide sequence encoding the fusion protein of the preceding paragraph. The polynucleotide sequence may be operably linked to a regulated promoter or a constitutive promoter. In another aspect, the present disclosure encompasses a vector comprising the polynucleotide sequence encoding the fusion protein. In another aspect, the present disclosure encompasses a host cell comprising the vector.

In another aspect, the present disclosure encompasses an isolated fusion protein comprising a kinase catalytic domain, an SH3 domain and a linker, wherein the kinase catalytic domain and the SH3 domain are joined by the linker. In certain embodiments the kinase catalytic domain is constitutively active. The isolated fusion protein may further comprise 1, 2, 3, 4, 5, 6, 7, 8, 9 or more peptide tags at either the N-terminus or the C-terminus, each independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a polynucleotide sequence encoding the fusion protein of the preceding paragraph. The polynucleotide sequence may be operably linked to a regulated promoter or a constitutive promoter. In another aspect, the present disclosure encompasses a vector comprising the polynucleotide sequence encoding the fusion protein. In another aspect, the present disclosure encompasses a host cell comprising the vector.

In another aspect, the present disclosure encompasses a polynucleotide sequence encoding a substrate protein, the substrate protein comprising a polypeptide of interest, a polyproline sequence, a protease cleavage site, and an optional linker. The polyproline sequence is at least 4 amino acids in length and contains the sequence proline-Xaa-Xaa-proline, wherein Xaa is any amino acid. Polylproline sequences with high, medium and low affinity for an SH domain are contemplated. In various embodiments, the polyproline sequence is capable of binding to an SH3 domain and has at least 80% sequence identity to a sequence selected from the group consisting of SEQ ID NO: 2, SEQ ID NO: 3, and SEQ ID NO: 4. The protease cleavage site is between the polypeptide of interest and the linker when the linker is present, and between the polypeptide of interest and the polyproline sequence when the linker is not present. The optional linker contains repeats of two, oppositely-charged, amino acids, and is about 10 to about 30 amino acids in length. The polynucleotide may further encode 1, 2, 3, 4, 5, 6, 7, 8, 9 or more peptide tags at either the N-terminus or the C-terminus of the substrate protein, each peptide tag independently selected from an affinity tag, a purification tag, a solubility tag, and a stability tag. In various embodiments, a fusion protein comprises (a) at least one affinity tag and/or at least one purification tag at the C-terminus and at least one stability tag or at least one solubility tag at the N-terminus, or (b) at least one affinity tag and/or at least one purification tag at the N-terminus of the fusion protein and at least one stability tag and/or solubility tag at the C-terminus. The isolated fusion protein may also comprise a protease cleavage site proximal to one or more of the peptide tags. In this manner, a peptide tag may be removed from the fusion protein upon cleavage by the cognate protease.

In another aspect, the present disclosure encompasses a kit for producing a post-translationally modified protein of interest, the kit comprising a first vector and a second vector, wherein (a) the first vector comprises a polynucleotide sequence encoding an SH3 domain, a linker, and a multiple cloning sequence, wherein the multiple cloning sequence is proximal to the linker and at the end of the linker opposite the SH3 domain, and the polynucleotide sequence is operably linked to a promoter; and (b) the second vector comprises a polynucleotide sequence encoding a polyproline sequence, protease cleavage site, and a multiple cloning sequence, wherein the multiple cloning sequence is proximal to protease cleavage site and at the end of the protease cleavage site opposite the polyproline sequence.

In another aspect, the present disclosure encompasses a kit for producing a phosphorylated protein of interest, the kit comprising a first vector and a second vector, wherein (a) the first vector comprises a polynucleotide sequence encoding an SH3 domain, a linker, and a multiple cloning sequence, wherein the multiple cloning sequence is proximal to the linker and at the end of the linker opposite the SH3 domain, and the polynucleotide sequence is operably linked to a promoter; and (b) the second vector comprises a polynucleotide sequence encoding a polyproline sequence, protease cleavage site, and a multiple cloning sequence, wherein the multiple cloning sequence is proximal to protease cleavage site and at the end of the protease cleavage site opposite the polyproline sequence.

In another aspect, the present disclosure encompasses a kit for producing a post-translationally modified protein of interest, the kit comprising a first vector and a second vector, wherein (a) the first vector comprises a polynucleotide sequence encoding an SH3 domain, a linker, and a catalytic domain of an enzyme involved in posttranslational modification, wherein the catalytic domain and the SH3 domain are joined by the linker, and the polynucleotide sequence is operably linked to a promoter; and (b) the second vector comprises a polynucleotide sequence encoding a polyproline sequence, protease cleavage site, and a multiple cloning sequence, wherein the multiple cloning sequence is proximal to protease cleavage site and at the end of the protease cleavage site opposite the polyproline sequence. In certain embodiments, the catalytic domain of an enzyme involved in posttranslational modification is a kinase catalytic domain or a constitutively active kinase catalytic domain.

Other aspects and iterations of the disclosure are described more thoroughly below.

REFERENCE TO COLOR FIGURES

The application file contains at least one photograph executed in color. Copies of this patent application publication with color photographs will be provided by the Office upon request and payment of the necessary fee.

Figure 2:
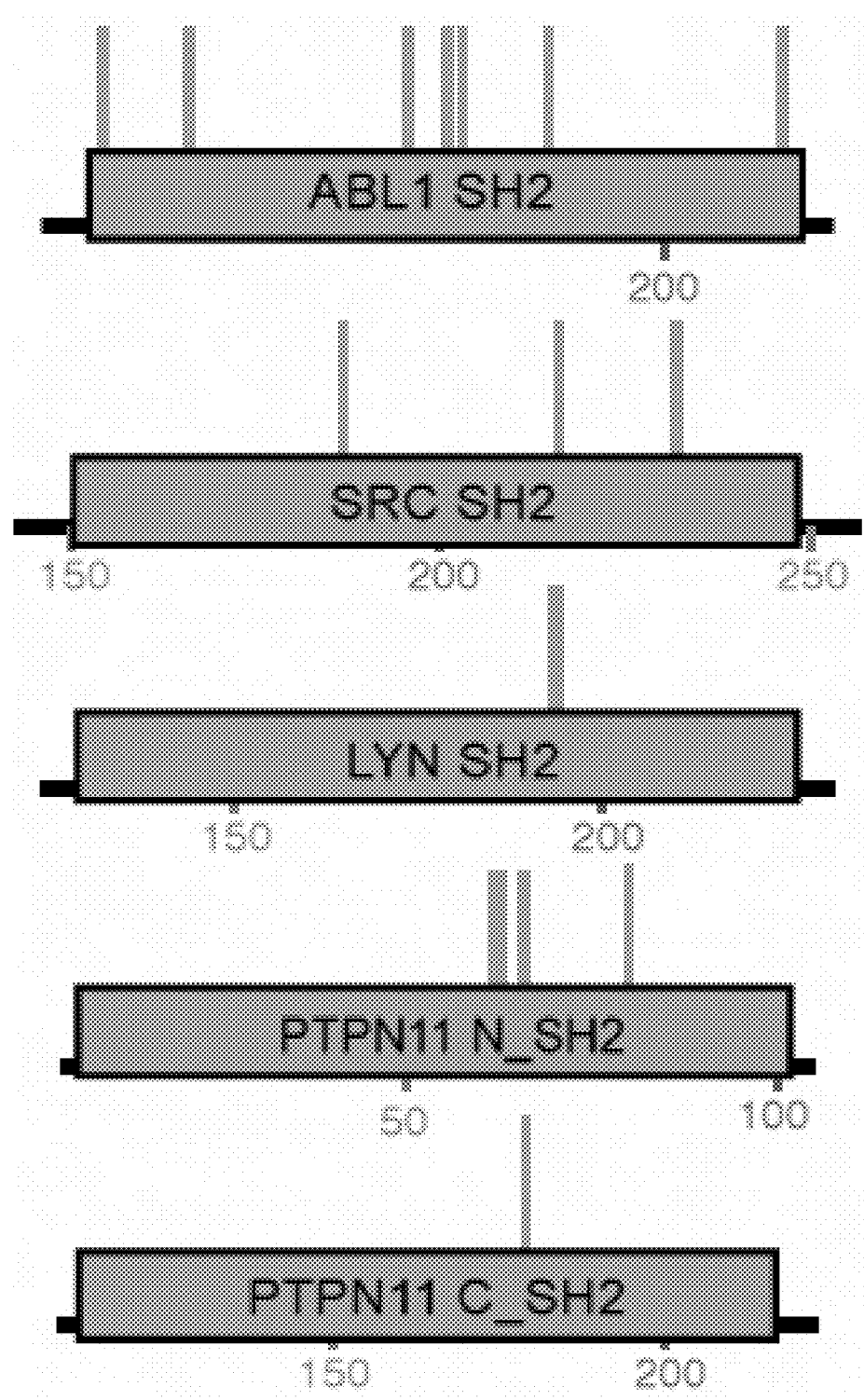

FIG. 1 illustrates the structural differences between a phosphotyrosine and a phosphomimic.

FIG. 2 illustrates ubiquitous phosphorylation on human SH2 domains. Specifically, the vertical bars represent known phosphotyrosines documented in the human proteome for five different SH2 domains—i.e. ABL1, SRC, LYN, PTPN11 N-terminal, and PTPN11 C-terminal. The figure is modified from ProteomeScout protein viewer export.

Figure 3:
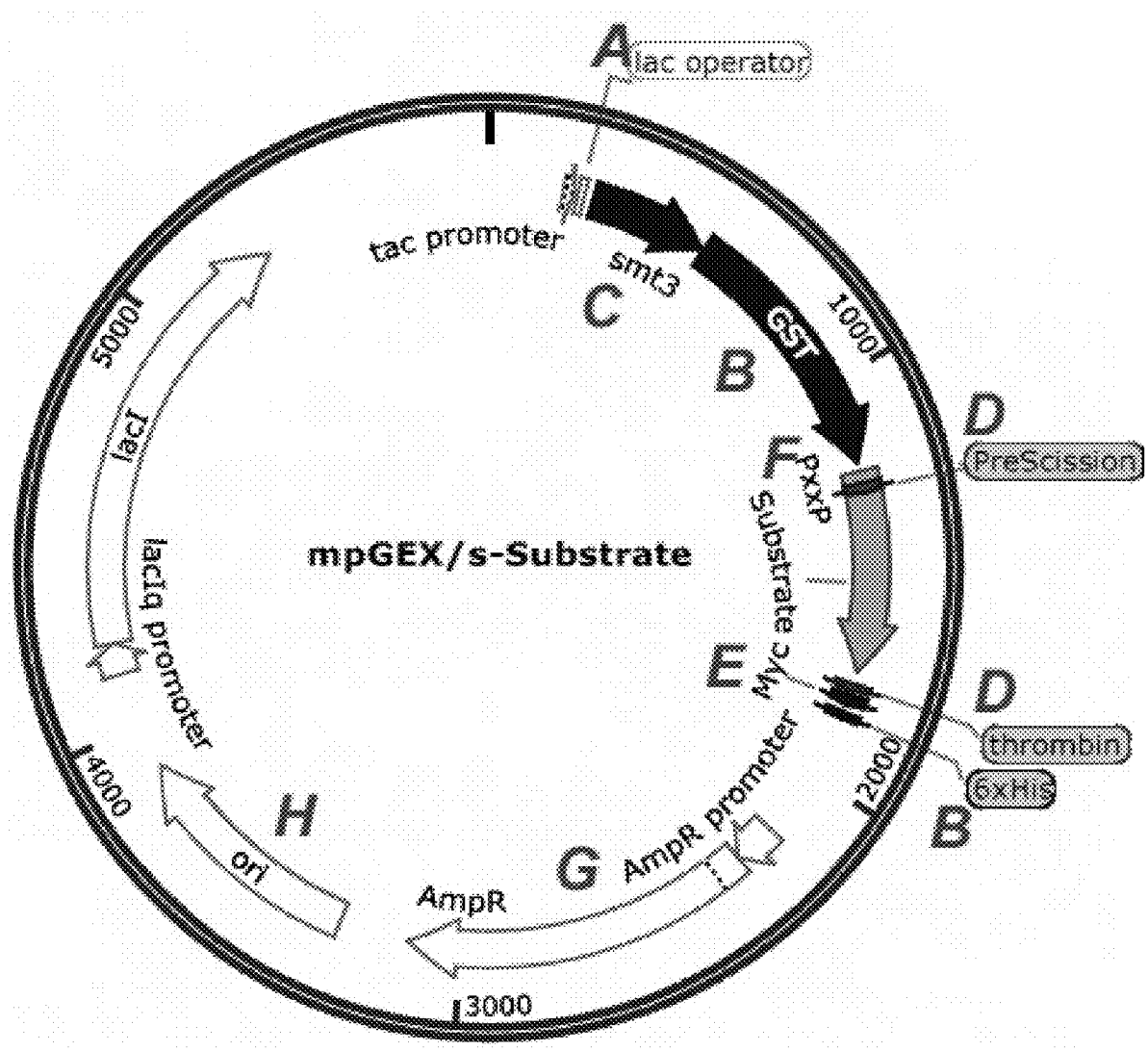

FIG. 3 is a map of a substrate protein vector. The various components of the vector are labeled. The label "PxxP" identifies the position of a polyproline sequence.

Figure 4:
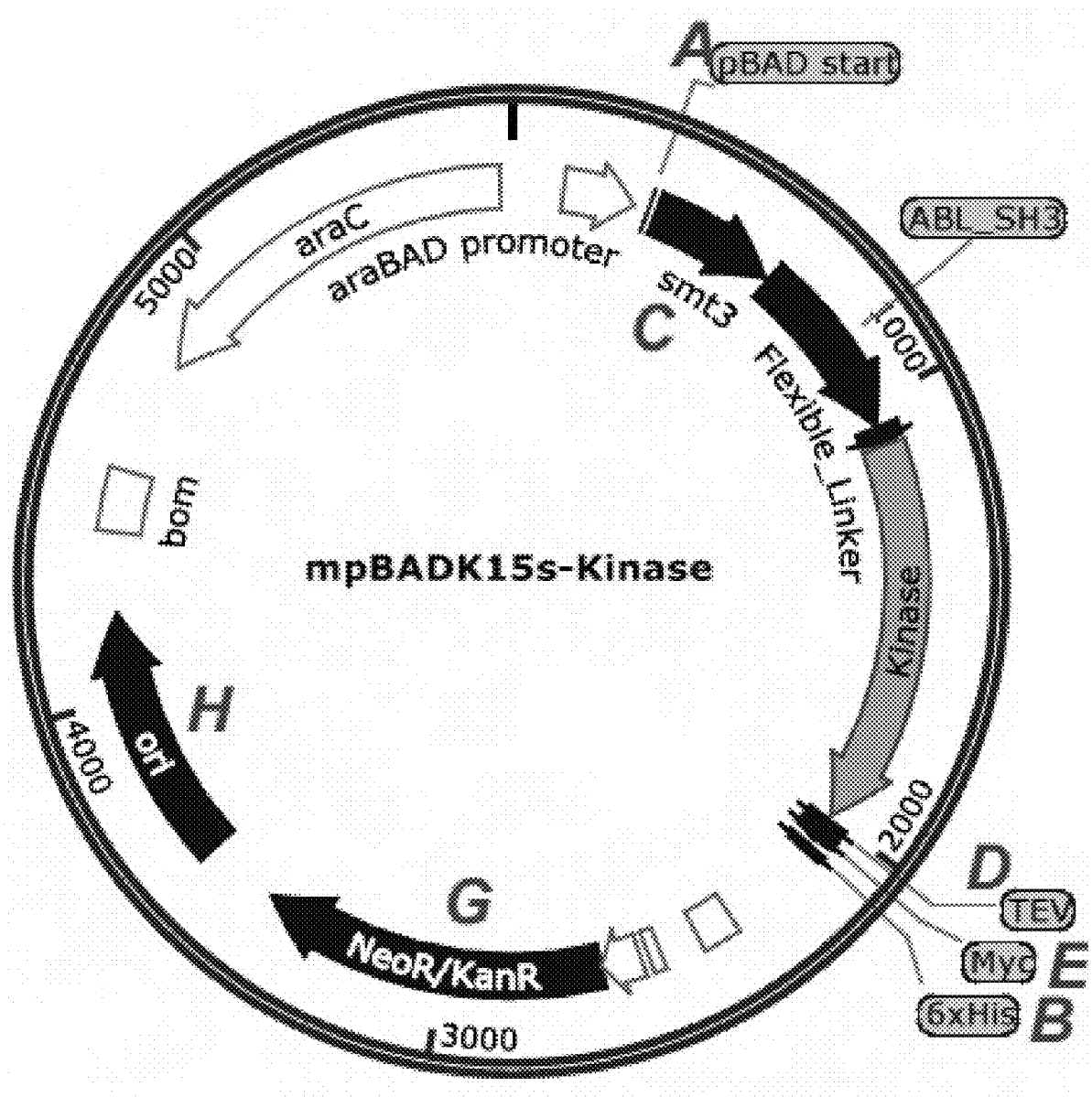

FIG. 4 is a map of a fusion protein vector. The various components of the vector are labeled. The label "kinase" identifies the position of a kinase or a kinase catalytic domain. The kinase domain may be replaced with alternative catalytic domains.

Figure 5:
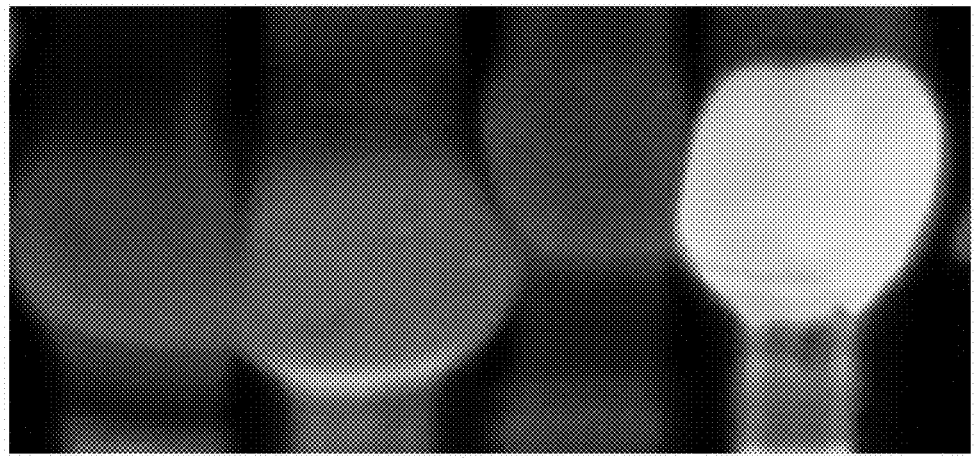

FIG. 5 depicts an image of a Western blot. A substrate protein comprising a polyproline sequence an ABL SH2 domain ("targeted substrate) and a protein comprising an ABL SH2 domain but lacking a polyproline sequence ("untargeted substrate") was incubated with crude cell lysate from a cell expressing a fusion protein comprising an constitutively active ABL kinase. The substrate protein was then purified (SN=supernatant before incubation with kinase and purification; E=elution following purification). Phosphorylation of the substrate protein was analyzed by Western blotting (red: anti-Myc; green: anti-phosphotyrosine). The leading edge of E in the untargeted sample indicates some phosphorylation of the untargeted substrate protein by the kinase. Comparison to E from the targeted sample shows that phosphorylation of the targeted substrate protein was significantly increased. This confirms the interaction between the SH3 domain of the fusion protein and the polyproline sequence of the substrate protein effectively targets the enzyme to its substrate, thereby increasing the amount of substrate modification.

Figure 6:
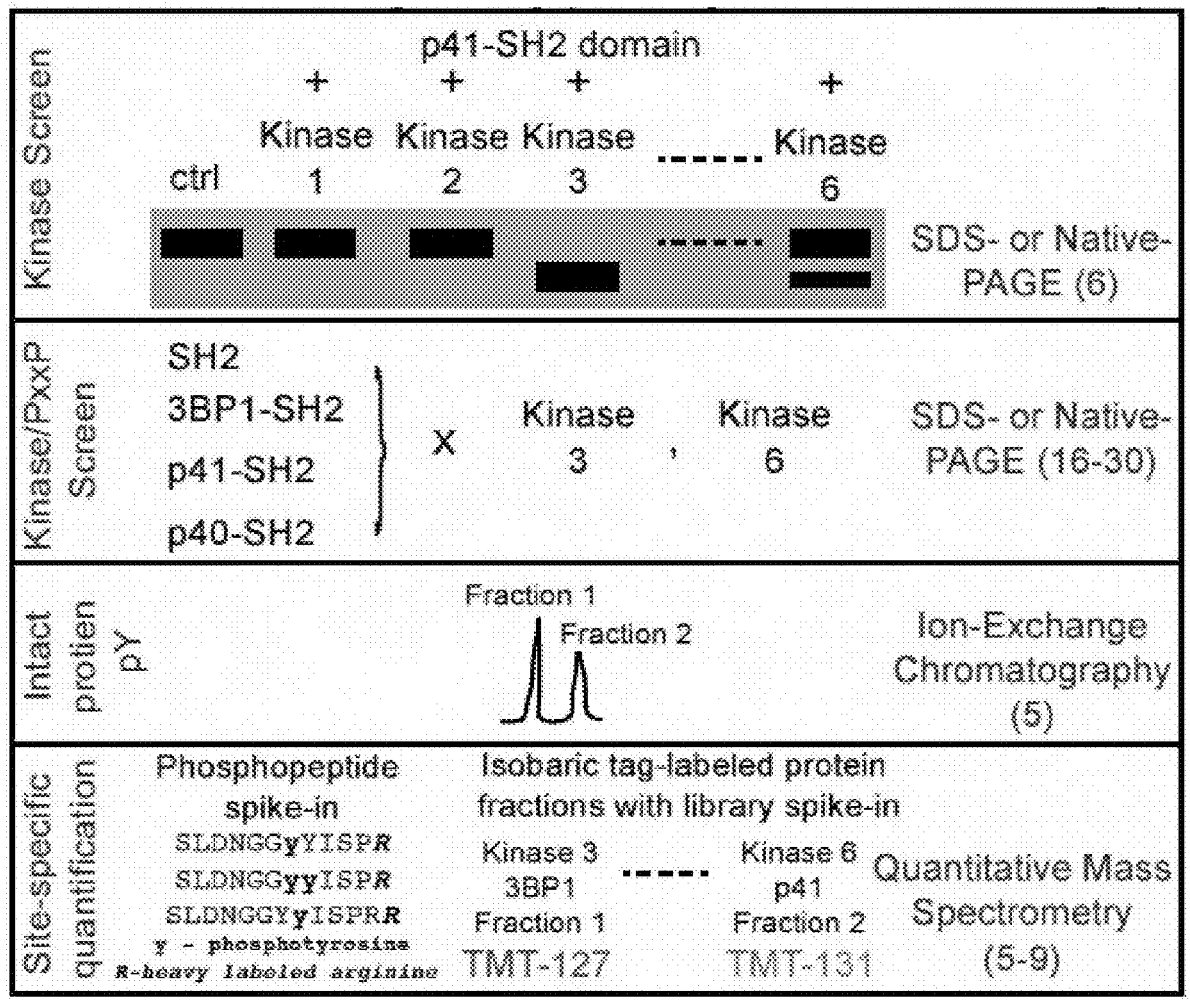

FIG. 6 depicts a workflow for identifying differential phosphorylation of SH2 domains as a function of kit components. The workflow moves from low resolution (top) to high resolution (bottom). The numbers in parentheses are an example of the number of samples estimated to be screened in each step (SEQ ID NOs:5-7).

DETAILED DESCRIPTION

The present disclosure provides a system to produce soluble, folded, and post-translationally modified proteins. The system includes a fusion protein comprising a catalytic domain of an enzyme involved in post-translational protein modification and a targeting domain, and a substrate protein comprising a protein of interest and a sequence that interacts with the targeting domain. When expressed together, or reacted in purified (or partially purified) form, the interaction between the enzyme and the substrate is augmented as a result of the interaction between the targeting domain and the sequence that interacts with the targeting domain. The combination of the engineered interaction's strength (i.e. targeting domain/sequence that interacts with the targeting domain) and catalytic specificity will determine the specific pattern of post-translational modification produced on the protein substrate. Control over the degree of modification for any given substrate is achieved by using sequences that interact with a targeting domain with different affinity for the targeting domain, different targeting domains, and/or different enzyme sequences. The present invention disclosure also provides polynucleotide sequences encoding fusion proteins and substrate proteins of this disclosure, vectors for expressing polynucleotide sequences of this disclosure, vectors comprising polynucleotide sequences of this disclosure, and isolated cells comprising said vectors. Each of these aspects is described more thoroughly below.

(a) Polynucleotide Sequence Encoding a Fusion Protein

In an aspect, the present disclosure provides a polynucleotide sequence encoding a fusion protein. A fusion protein comprises a catalytic domain, or a variant thereof, of an enzyme involved in post-translational protein modification, a targeting domain, and optionally a linker that joins the catalytic domain and the targeting domain. A polynucleotide sequence encoding a fusion protein may further encode a signal peptide, at least one N-terminal peptide tag, at least one C-terminal peptide tag, at least one protease cleavage site, and any combination thereof.

(i) Catalytic Domain of an Enzyme Involved in Post-Translational Protein Modification A fusion protein comprises a catalytic domain of an enzyme involved in post-translational protein modification. As used herein, the term "catalytic domain" refers to a region, or regions, of an enzyme that form the active or functional site of the enzyme and any portion necessary for catalytic activity. In some embodiments, a fusion protein comprises only a catalytic domain. In other embodiments, a fusion protein comprises the mature form of an enzyme. As used herein, the term "mature form" refers to the amino acid sequence of an enzyme after any post-translational cleavage of signal peptides. Non-limiting examples of enzymes involved in post-translational protein modification include kinases, phosphatases, ubiquitin ligases, SUMO ligases, methyltransferases, demethylases, acetyltransferases, deacetylases, lipid transferases (e.g. N-myristoyltransferase, palmitoyl acyl Transferases, farnesyl transferase, geranylgeranyl transferases), enzymes involved in glycosylation, etc. A more comprehensive list of protein modifications and the enzymes responsible therefore can be found in the art. For example, see Krishna et al. "Identification of common post-translational modifications." In: Creighton T. E., editor. *Protein structure: A practical approach*. Oxford: Oxford University Press; 1997. pp. 91-116.

In each of the above embodiments, a fusion protein may comprise a variant catalytic domain. A variant catalytic domain may be constitutively active, have increased stability, increased catalytic activity, increased processivity, increased affinity for its substrate, or any combination thereof. In an exemplary embodiment, a variant catalytic domain is constitutively active.

In preferred embodiments, the catalytic domain is a kinase domain. As used herein, the term "kinase catalytic domain" or "kinase domain" refers to a region, or region(s), of a protein kinase that transfers a phosphate to one or more amino acid residue in a protein substrate. Catalytic subunits of protein kinases are highly conserved, and well known in the art. A kinase domain may phosphorylate a substrate protein on an amino acid selected from the group consisting of a serine (i.e. "a serine kinase catalytic domain"), a threonine, a tyrosine, a histidine, an aspartate, or a combination thereof. A kinase may be categorized or described with respect to substrate specificity. For example, a kinase may be generally described as a serine/threonine-protein kinase, a tyrosine-protein kinase, a histidine/aspartate kinase, or dual specificity kinase (e.g. capable of phosphorylating across groups). Non-limiting examples of human proteins containing a kinase catalytic domain include AAK1; ABL1; ABL2; ACVR1; ACVR1B; ACVR1C; ACVR2A; ACVR2B; ACVRL1; ADCK1; ADCK2; ADCK3; ADCK4; ADCK5; ADRBK1; ADRBK2; AKT1; AKT2; AKT3; ALPK1; ALPK2; ALPK3; STRADB; CDK15; AMHR2; ANKK1; ARAF; ATM; ATR; AURKA; AURKB; AURKC; AXL; BCKDK; BLK; BMP2K; BMPR1A; BMPR1B; BMPR2; BMX; BRAF; BRSK1; BRSK2; BTK; BUB1; C21orf7; CALM1; CALM2; CALM3; CAMK1; CAMK1 D; CAMK1G; CAMK2A; CAMK2B; CAMK2D; CAMK2G; CAMK4; CAMKK1; CAMKK2; CAMKV; CASK; CDK20; CDK1; CDK11B; CDK11A; CDK13; CDK19; CDC142BPA; CDCl$_2$BPB; CDCl$_2$BPG; CDCl$_7$; CDK10; CDK2; CDK3; CDK4; CDK5; CDK6; CDK7; CDK8; CDK9; CDK12; CDK14; CDK16; CDK17; CDK18; CDKL1; CDKL2; CDKL3; CDKL4; CDKL5; CHEK1; CHEK2; CHUK; CIT; CKB; CKM; CLK1; CLK2; CLK3; CLK4; CSF1R; CSK; CSNK1A1; CSNK1A1L; CSNK1D; CSNK1E; CSNK1G1; CSNK1G2; CSNK1G3; CSNK2A1; CSNK2A2; DAPK1; DAPK2; DAPK3; DCLK1; DCLK2; DCLK3; DDR1; DDR2; DMPK; DYRK1A; DYRK1B; DYRK2; DYRK3; DYRK4; EGFR; EIF2AK1; EIF2AK2; EIF2AK3; EIF2AK4; ELK1; EPHA1; EPHA2; EPHA3; EPHA4; EPHA5; EPHA6; EPHA7; EPHA8; EPHB1; EPHB2; EPHB3; EPHB4; ERBB2; ERBB3; ERBB4; ERN1; ERN2;

FER; FES; FGFR1; FGFR2; FGFR3; FGFR4; FGR; FLT1; FLT3; FLT4; FYN; GAK; GRK1; GRK4; GRK5; GRK6; GRK7; GSK3A; GSK3B; GUCY2C; GUCY2D; GUCY2E; GUCY2F; HCK; HIPK1; HIPK2; HIPK3; HIPK4; HUNK; ICK; IGF1R; IGF2R; IKBKB; IKBKE; ILK; INSR; IRAK1; IRAK2; IRAK3; IRAK4; ITK; JAK1; JAK2; JAK3; KALRN; KDR; SIK3; KSR2; LATS1; LATS2; LIMK1; LCK; LIMK2; LRRK1; LRRK2; LYN; MAK; MAP2K1; MAP2K2; MAP2K3; MAP2K4; MAP2K5; MAP2K6; MAP2K7; MAP3K1; MAP3K10; MAP3K11; MAP3K12; MAP3K13; MAP3K14; MAP3K15; MAP3K2; MAP3K3; MAP3K4; MAP3K5; MAP3K6; MAP3K7; MAP3K8; MAP3K9; MAP4K1; MAP4K2; MAP4K3; MAP4K4; MAP4K5; MAPK1; MAPK10; MAPK12; MAPK13; MAPK14; MAPK15; MAPK3; MAPK4; MAPK6; MAPK7; MAPK8; MAPK9; MAPKAPK2; MAPKAPK3; MAPKAPK5; MARK1; MARK2; MARK3; MARK4; MAST1; MAST2; MAST3; MAST4; MASTL; MELK; MERTK; MET; MINK1; MKNK1; MKNK2; MLKL; MOS; MST1R; MST4; MTOR; MYLK; MYLK2; MYLK3; MYLK4; NEK1; NEK10; NEK11; NEK2; NEK3; NEK4; NEK5; LOC100506859; NEK6; NEK7; NEK8; NEK9; MGC42105; NLK; NRK; NTRK1; NTRK2; NTRK3; NUAK1; NUAK2; OBSCN; OXSR1; PAK1; PAK2; PAK3; PAK4; PAK6; PAK7; PASK; PBK; PDGFRA; PDGFRB; PDIK1L; PDPK1; PHKA1; PHKB; PHKG1; PHKG2; PIK3R4; PIM1; PIM2; PIM3; PINK1; PKMYT1; PKN1; PKN2; PKN3; PLK1; PLK2; PLK3; PLK4; PNCK; PRKAA1; PRKAA2; PRKACA; PRKACB; PRKACG; PRKCA; PRKCB; PRKCD; PRKCE; PRKCG; PRKCH; PRKCI; PRKCQ; PRKCZ; PRKD1; PRKD2; PRKD3; PRKG1; PRKG2; PRKX; LOC389906; PRKY; PRPF4B; PSKH1; PSKH2; PTK2; PTK2B; RAF1; RAGE; RET; RIP3; RIPK1; RIPK2; RIPK3; RIPK4; ROCK1; ROCK2; ROR1; ROR2; ROS1; RPS6KA1; RPS6KA2; RPS6KA3; RPS6KA4; RPS6KA5; RPS6KA6; RPS6KB1; RPS6KB2; RPS6KC1; RPS6KL1; RYK; SCYL1; SCYL2; SCYL3; SGK1; LOC100130827; SGK196; SGK2; SGK3; SGK494; SIK1; SIK2; SLK; SNRK; SPEG; SRC; SRPK1; SRPK2; SRPK3; STK10; STK11; STK16; STK17A; STK17B; STK19; STK24; STK25; STK3; STK31; STK32A; STK32B; STK32C; STK33; STK35; STK36; STK38; STK38L; STK39; STK4; STK40; SYK; TAOK1; TAOK2; TAOK3; TBCK; TBK1; TEC; TESK1; TESK2; TGFBR1; TGFBR2; TIE1; TIE2; TLK1; TLK2; TNIK; TNK1; TNK2; TSSK1B; TSSK2; TSSK3; TSSK4; TTBK1; TTBK2; TTK; TWF2; TXK; TYK2; TYRO3; UHMK1; ULK1; ULK2; ULK3; ULK4; VRK1; VRK2; VRK3; WEE1; WEE2; WNK1; WNK2; WNK3; WNK4; YES1; ZAK; and ZAP70. Polynucleotide and amino acid sequences encoding protein kinases, including those listed above, are also know in the art. For example, polynucleotide and amino acid sequences may be found in the NCBI Reference Sequence Database by searching the protein or gene name. In certain embodiments, the kinase is selected from FAK, EGFR, BTK, SRC, ABL, JAK, MET, and EphA4. In certain embodiments, the kinase is selected from FAK, EGFR, BTK, JAK, MET, and EphA4. In certain embodiments, the kinase is selected from SRC and ABL. In certain embodiments, the kinase is selected from EGFR, JAK, and MET.

In an exemplary embodiment, the catalytic domain is constitutively active. Constitutively-active kinase domains are known in the art and commercially available. Alternatively, one skilled in the art may generate a kinase that is constitutively active through routine experimentation as described in the art. In certain embodiments, the constitutively-active kinase is selected from FAK, EGFR, BTK, SRC, ABL, JAK, MET, and EphA4. In certain embodiments, the constitutively-active kinase is selected from FAK, EGFR, BTK, JAK, MET, and EphA4. In certain embodiments, the constitutively-active kinase is selected from SRC and ABL. In certain embodiments, the constitutively-active kinase is selected from EGFR, JAK, and MET.

(ii) Targeting Domain

A fusion protein also comprises a targeting domain. As used herein, a "targeting domain" associates, using at least two amino acid residues, with at least one peptide or polypeptide, or nucleic acid. The targeting domain and the at least one peptide, polypeptide, or polynucleotide may interact with each other through covalent and/or non-covalent associations. Non-limiting examples of targeting domains include coiled coil domains, acid patch domains, zinc finger domains, calcium hand domains, $C_H 1$-$C_L$ pair domains, leucine zipper domains, the yeast transcriptional activator GCN4, SH2 (src homology 2), SH3 (src Homology 3), phosphotyrosine binding (PTB) domains, WW domain, PDZ domain, 14-3-3 domain, WD40 domain, EH domain, Lim domain, an isoleucine zipper domain, a receptor dimer pair, and integrin heterodimers and can also be variants of these domains in which the affinity is altered. Additional targeting domains may be determined by measuring protein-protein interactions or protein-nucleic acid interactions. Methods to determine protein-protein interactions are known in the art and may include co-immunoprecipitation, biomolecular fluorescence complementation (BiFC), affinity electrophoresis, pull-down assays, label transfer, yeast two-hybrid, phage display, in vivo crosslinking, tandem affinity purification (TAP), chemical crosslinking, strep protein interaction experiment (SPINE), quantitative immunoprecipitation combined with knock-down (QUICK), proximity ligation assay (PLA), bio-layer interferometry, dual polarization interferometry (DPI), static light scattering (SLS), dynamic light scattering (DLS), surface plasmon resonance, fluorescence polarization/anisotropy, fluorescence correlation spectroscopy, fluorescence resonance energy transfer (FRET), NMR, protein-protein docking, isothermal titration calorimetry (ITC), and microscale thermophoresis (MST).

In a specific embodiment, the targeting domain is a SH3 domain. As used herein, the term "SH3 domain" refers to a SRC Homology 3 domain. An SH3 domain has a characteristic beta-barrel fold that consists of five or six β-strands arranged as two tightly packed anti-parallel β sheets. The linker regions may contain short helices. An SH3 domain is typically about 50 to about 60 amino acids in length. SH3 domains are well known in the art. See, for example, Pawson T, Schlessingert J (July 1993). "SH2 and SH3 domains". Curr. Biol. 3 (7): 434-42; Mayer BJ (April 2001). "SH3 domains: complexity in moderation". J. Cell. Sci. 114 (Pt 7): 1253-63; Musacchio A, Gibson T, Lehto V P, Saraste M (July 1992). "SH3—an abundant protein domain in search of a function". FEBS Lett. 307 (1): 55-61; Mayer B J, Baltimore D (January 1993). "Signalling through SH2 and SH3 domains". Trends Cell Biol. 3 (1): 8-13; Pawson T (February 1995). "Protein modules and signalling networks". Nature 373 (6515): 573-80; or Whisstock J C, Lesk A M (April 1999). "SH3 domains in prokaryotes". Trends Biochem. Sci. 24 (4): 132-3; each hereby incorporated by reference in its entirety. In an exemplary embodiment, an SH3 domain is an ABL SH3 domain or a derivative thereof.

The targeting domain may be N-terminal or C-terminal to the catalytic domain. In some embodiments, the targeting domain is on the N-terminal side of the catalytic domain. In other embodiments, the targeting domain is on the C-terminal side of the catalytic domain.

(iii) Linker

A fusion protein may comprise a linker. The optional linker is flexible and contains repeats of two, oppositely-charged, amino acids. The charging pattern creates a linker that is more likely to be extended than a traditional repeat of alanines or glycines, but less likely to create a rigid extension as would occur with the inclusion of proline. The linker improves targeting domain and kinase domain separation. Typically, each repeat of the linker contains the same two amino acids. The linker length can vary but is generally between about 10 to about 30 amino acids in length. In an exemplary embodiment, the amino acid residues of the repeat are lysine and aspartic acid.

(iv) Peptide Tag

A fusion protein may further comprise a peptide tag. A peptide tag can be an affinity tag, a purification tag, a solubility tag, a stability tag, or a detection tag. A peptide tag may have more than one utility—e.g. a peptide tag may be both an affinity tag and a purification tag. Suitable affinity tags, purification tags, solubility tags, stability tags, or detection tags are well known in the art and commercially available. A non-limiting list of suitable peptide tags is provided in the table below. The functions attributed to each tag in the table are not limiting.

TABLE A

| Tag | Exemplary Function |
|---|---|
| CBP | Affinity and Purification |
| FLAG | Affinity and Purification |
| GST | Purification and Stability |
| HA | Affinity |
| HBH | Affinity and Purification |
| MBP | Solubility and Purification |
| Myc | Affinity |
| poly His (e.g. hexahistidine) | Affinity and Purification |
| S-tag | Solubility and Affinity |
| SUMO | Stability |
| TAP | Affinity and Purification |
| TRX | Solubility |
| V5 | Affinity and Purification |
| GFP and other fluorescent proteins | Detection and Purification |
| AviTag ™ | Purification |
| SBP | Purification |
| Strep | Purification |
| Polyarginine | Purification |
| Polyglutamine | Purification |

In some embodiments, a polynucleotide sequence encoding a fusion protein further encodes at least one N-terminal peptide tag. In other embodiments, a polynucleotide sequence encoding a fusion protein further encodes at least one C-terminal peptide tag. In still other embodiments, a polynucleotide sequence encoding a fusion protein further encodes at least one N-terminal peptide tag and at least one C-terminal peptide tag. In each of the above embodiments, a polynucleotide sequence encoding a fusion protein may encode 1, 2, 3, 4, 5, 6, 7, 8, 9 or more peptide tags, each independently selected from an affinity tag, a purification tag, a solubility tag, and a stability tag. In an exemplary embodiment, a polynucleotide sequence encoding a fusion protein further encodes (a) at least one affinity tag and/or at least one purification tag, and (b) at least one solubility tag and/or at least one stability tag. In another exemplary embodiment, a polynucleotide sequence encoding a fusion protein further encodes (a) at the C-terminus of the fusion protein, at least one affinity tag and/or at least one purification tag, and (b) at the N-terminus of the fusion protein, at least one stability tag or at least one solubility tag. In yet another exemplary embodiment, a polynucleotide sequence encoding a fusion protein further encodes (a) at the N-terminus of the fusion protein, at least one affinity tag and/or at least one purification tag, and (b) at the C-terminus of the fusion protein, at least one stability tag and/or solubility tag.

(v) Protease Cleavage Site

The fusion protein may comprise a protease cleavage site. Non-limiting examples of protease cleavage sites include a tomato etch virus (TEV) protease cleavage site, a thrombin cleavage site, a PreScisison cleavage site, or variants thereof. The amino acid sequences of these protease cleavage sites are known in art, as are additional protease cleavage sites suitable for, and commonly used in, vectors. In addition, the peptide tags SUMO and FLAG are cleaved by specific proteases without requiring the addition of an independent cleavage recognition site.

In embodiments comprising at least one peptide tag, the fusion protein may further comprise a protease cleavage site proximal to one or more of the peptide tags. In this manner, a peptide tag may be removed from the fusion protein upon cleavage by the cognate protease. However, it is not necessary that a protease cleavage site be present for each peptide tag.

(vi) Signal Peptide

In any of the above embodiments, the polynucleotide sequence may encode a signal peptide. When present, the signal peptide is typically at the N-terminus of the fusion protein. The choice of polynucleotide sequence encoding the signal peptide can and will vary depending on a variety factors including, but not limited to, the type of cell, the desired cellular location, or whether the protein is to be secreted from the cell. For example, in certain embodiments it may be desirable to use a secretory signal peptide in order to target a fusion protein outside a host cell for purification from the culture supernatant. Alternatively, it certain embodiments it may be desirable to target a fusion protein to a particular organelle in a eukaryotic host cell (e.g. an endosome, or a nucleus, etc.) via a localization signal peptide. Suitable polynucleotide sequences encoding signal peptides are known in the art, as are polypeptide sequences encoded therefrom.

(b) Polynucleotide Sequence Encoding a Substrate Protein

In another aspect, the present disclosure provides a polynucleotide sequence encoding a substrate protein. A substrate protein comprises a protein of interest, a sequence that interacts with the targeting domain, and an optional linker. A polynucleotide sequence encoding a substrate protein may further encode a signal peptide, at least one N-terminal peptide tag, at least one C-terminal peptide tag, at least one protease cleavage site, and any combination thereof.

(i) Protein of Interest

A substrate protein comprises a protein of interest. The term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The type of protein is not a limiting feature of this disclosure. Generally, a protein of interest is known substrate, or believed to be a substrate, of an enzyme, in particular the enzyme comprising the fusion protein.

In some embodiments, a protein of interest is an SH2 domain. In other embodiments, a protein of interest is an antibody, an antibody fragment, or a single-chain, antigen-binding protein (e.g. scFv, di-scFv, bi-scFv, etc.). In other embodiments, a protein of interest is a therapeutic protein (i.e. a "biological product"). In other embodiments, a protein of interest is a catalytically inactive form of a kinase.

In an exemplary embodiment, a protein of interest is capable of being phosphorylated by a kinase catalytic domain. For example, if the kinase catalytic domain is serine/threonine-protein kinase catalytic domain, a suitable substrate protein has at least one serine and/or threonine that can be phosphorylated by the kinase catalytic domain. Similarly, if the kinase catalytic domain is a tyrosine-protein kinase catalytic domain, a suitable substrate protein has at least one tyrosine that can be phosphorylated by the kinase catalytic domain. Alternatively, if the kinase catalytic domain is a histidine/aspartate kinase catalytic domain, a suitable substrate protein has at least one histidine or aspartate that can be phosphorylated by the kinase catalytic domain.

(ii) Sequence that Interacts with the Targeting Domain

A substrate protein comprises a sequence that interacts with the targeting domain. As described above, a targeting domain may be a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair. Accordingly, a sequence that interacts with a targeting domain is any sequence that interacts with a coiled-coil domain, an acid patch, a zinc finger domain, a calcium hand domain, a CHI region, a CL region, a leucine zipper domain, an SH2 (src homology 2) domain, an SH3 (src Homology 3) domain, a PTB (phosphotyrosine binding) domain, a WW domain, a PDZ domain, a 14-3-3 domain, a WD40 domain, an EH domain, a Lim domain, an isoleucine zipper domain, and a dimerization domain of a receptor dimer pair. It is within the skill of one in the art to identify the sequences that interact with a targeting domain. Sequences that interact with a targeting domain may be determined by measuring protein-protein or protein-nucleic acid interactions. Methods to determine protein-protein interactions are known in the art and may include co-immunoprecipitation, biomolecular fluorescence complementation (BiFC), affinity electrophoresis, pull-down assays, label transfer, yeast two-hybrid, phage display, in vivo crosslinking, tandem affinity purification (TAP), chemical crosslinking, strep protein interaction experiment (SPINE), quantitative immunoprecipitation combined with knock-down (QUICK), proximity ligation assay (PLA), bio-layer interferometry, dual polarization interferometry (DPI), static light scattering (SLS), dynamic light scattering (DLS), surface plasmon resonance, fluorescence polarization/anisotropy, fluorescence correlation spectroscopy, fluorescence resonance energy transfer (FRET), NMR, protein-protein docking, isothermal titration calorimetry (ITC), and microscale thermophoresis (MST).

Specifically the sequence that interacts with the targeting domain is an amino acid sequence comprising two or more amino acid residues that interact with the targeting domain, or a nucleic acid sequence comprising two or more nucleic acids that interact with the targeting domain. The sequence that interacts with the targeting domain may interact through covalent or non-covalent associations. A sequence that interacts with a targeting domain may be at least 4, 5, 6, 7, 8, 9, 10, 11, 12, 13, 14, 15, 16, 17, 18, 19, 20, 21, 22, 23, 24, 25, 26, 27, 28, 29, 30 or more amino acids in length. A sequence that interacts with a targeting domain may be about 5 to about 10, about 6 to about 11, about 7 to about 12, about 8 to about 13, about 9 to about 14, about 10 to about 15, about 15 to about 20, about 20 to about 25, about 25 to about 30, about 5 to about 15, about 10 to about 25, or about 5 to about 20 amino acids in length. A sequence that interacts with a targeting domain is capable of binding to a targeting domain with high affinity (e.g. a $K_D$ less than about 0.5 µM). In other embodiments, a sequence that interacts with a targeting domain is capable of binding to a targeting domain with medium affinity (e.g. a $K_D$ of about 0.5 µM to about 5 µM). In still other embodiments, a sequence that interacts with a targeting domain is capable of binding to a targeting domain with low affinity (e.g. a $K_D$ greater than about 5 µM).

In a specific embodiment, a substrate protein comprises a polyproline sequence that is capable of binding to an SH3 domain. As used herein, the term "polyproline sequence" refers to an amino acid sequence comprising SEQ ID NO: 1. A polyproline sequence may be at least 4, 5, 6, 7, 8, 9, 10, 11, 12, 13, 14, 15, 16, 17, 18, 19, 20, 21, 22, 23, 24, 25, 26, 27, 28, 29, 30 or more amino acids in length. A polyproline sequence may be about 5 to about 10, about 6 to about 11, about 7 to about 12, about 8 to about 13, about 9 to about 14, about 10 to about 15, about 15 to about 20, about 20 to about 25, about 25 to about 30, about 5 to about 15, about 10 to about 25, or about 5 to about 20 amino acids in length.

Polyproline sequences capable of binding SH3 domains are known in the art. See, for example, Weng et al. *Mol Cell Biol* 1995, 15(10)5627-5634, hereby incorporated by reference in its entirety. SH3 domains bind polyproline sequences with affinities ($K_D$) generally in the order of about 0.2 µM to about 50 µM, and methods are known in the art that allow for the rational design of polyproline sequence variants with modified (i.e. increased or decreased) affinity for any given SH3 domain. See, for example, Pisabarro et al. *Biochemistry* 1996, 35(33):10634-10640; or Pisabarro et al. *J Mol Biol* 1998, 281:513-521; each hereby incorporated by reference in its entirety.

In certain embodiments, a polyproline sequence is capable of binding to an SH3 domain with high affinity (e.g. a $K_D$ less than about 0.5 µM). In other embodiments, a polyproline sequence is capable of binding to an SH3 domain with medium affinity (e.g. a $K_D$ of about 0.5 µM to about 5 µM). In still other embodiments, a polyproline sequence is capable of binding to an SH3 domain with low affinity (e.g. a $K_D$ greater than about 5 µM).

In an exemplary embodiment, a polyproline sequence is capable of binding to an SH3 domain and has at least 80% sequence identity to a sequence selected from the group consisting of SEQ ID NO: 2, SEQ ID NO: 3, and SEQ ID NO: 4. For example, a polyproline sequence may have at least 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 2, SEQ ID NO: 3, or SEQ ID NO: 4. In another exemplary embodiment, a polyproline sequence is capable of binding to an SH3 domain and has at least 85% sequence identity to a sequence selected from the group consisting of SEQ ID NO: 2, SEQ ID NO: 3, and SEQ ID NO: 4. In other embodiments, a polyproline sequence is capable of binding to an SH3 domain and has at least 90% sequence identity to a sequence selected from the group consisting of SEQ ID NO: 2, SEQ ID NO: 3, and SEQ ID NO: 4. In still another exemplary embodiment, a polyproline sequence is capable of binding to an SH3 domain and has at least 95% sequence identity to a sequence selected from the group consisting of SEQ ID NO: 2, SEQ ID NO: 3, and SEQ ID NO: 4. In yet another exemplary embodiment, a polyproline sequence is capable of binding to an SH3 domain and has a sequence selected from the group consisting of SEQ ID NO: 2, SEQ ID NO: 3, and SEQ ID NO: 4.

(iii) Linker

A substrate protein may comprise a linker. The optional linker is flexible and contains repeats of two, oppositely-charged, amino acids. The charging pattern creates a linker that is more likely to be extended than a traditional repeat of alanines or glycines, but less likely to create a rigid extension as would occur with the inclusion of proline. The linker results in improved protein of interest and sequence that interacts with a targeting domain separation. Typically, each repeat of the linker contains the same two amino acids. The linker length can vary but is generally between about 10 to about 30 amino acids in length. In an exemplary embodiment, the amino acid residues of the repeat are lysine and aspartic acid.

(iv) Peptide Tag

A substrate protein may further comprise a peptide tag. A peptide tag can be an affinity tag, a purification tag, a solubility tag, a stability tag, or a detection tag. A peptide tag may have more than one utility—e.g. a peptide tag may be both an affinity tag and a purification tag. Suitable affinity tags, purification tags, solubility tags, stability tags, or detection tags are well known in the art and commercially available. A non-limiting list of suitable peptide tags is provided in Table A. The functions attributed to each tag in Table A are not limiting.

In some embodiments, a polynucleotide sequence encoding a substrate protein further encodes at least one N-terminal peptide tag. In other embodiments, a polynucleotide sequence encoding a substrate protein further encodes at least one C-terminal peptide tag. In still other embodiments, a polynucleotide sequence encoding a substrate protein further encodes at least one N-terminal peptide tag and at least one C-terminal peptide tag. In each of the above embodiments, a polynucleotide sequence encoding a substrate protein may encode 1, 2, 3, 4, 5, 6, 7, 8, 9 or more peptide tags, each independently selected from an affinity tag, a purification tag, a solubility tag, and a stability tag. In an exemplary embodiment, a polynucleotide sequence encoding a substrate protein further encodes (a) at least one affinity tag and/or at least one purification tag, and (b) at least one solubility tag and/or at least one stability tag. In another exemplary embodiment, a polynucleotide sequence encoding a substrate protein further encodes (a) at the C-terminus of the substrate protein, at least one affinity tag and/or at least one purification tag, and (b) at the N-terminus of the substrate protein, at least one stability tag or at least one solubility tag. In yet another exemplary embodiment, a polynucleotide sequence encoding a substrate protein further encodes (a) at the N-terminus of the substrate protein, at least one affinity tag and/or at least one purification tag, and (b) at the C-terminus of the substrate protein, at least one stability tag and/or solubility tag.

(v) Protease Cleavage Site

A substrate protein may comprise a protease cleavage site. Non-limiting examples of protease cleavage sites include a tomato etch virus (TEV) protease cleavage site, a thrombin cleavage site, a PreScisison cleavage site, or variants thereof. The amino acid sequences of these protease cleavage sites are known in art, as are additional protease cleavage sites suitable for, and commonly used in, vectors. In addition, the peptide tags SUMO and FLAG are cleaved by specific proteases without requiring the addition of an independent cleavage recognition site.

In certain embodiments, a substrate protein may further comprise a protease cleavage site proximal to the sequence that interacts with the targeting domain or the linker. And in embodiments comprising at least one peptide tag, the substrate protein may further comprise a protease cleavage site proximal to one or more of the peptide tags. In this manner, the sequence that interacts with the targeting domain and any peptide tags may be removed from the substrate protein upon cleavage by the cognate protease. However, it is not necessary that a protease cleavage site be present for each peptide tag.

(vi) Signal Peptide

In any of the above embodiments, the polynucleotide sequence may encode a signal peptide. When present, the signal peptide is typically at the N-terminus of the substrate protein. The choice of polynucleotide sequence encoding the signal peptide can and will vary depending on a variety factors including, but not limited to, the type of cell, the desired cellular location, or whether the protein is to be secreted from the cell. For example, in certain embodiments it may be desirable to use a secretory signal peptide in order to target a substrate protein outside a host cell for purification from the culture supernatant. Alternatively, it certain embodiments it may be desirable to target a substrate protein to a particular organelle in a eukaryotic host cell (e.g. an endosome, or a nucleus, etc.) via a localization signal peptide. Suitable polynucleotide sequences encoding signal peptides are known in the art, as are polypeptide sequences encoded therefrom.

(c) Vector

In another aspect, the present disclosure also provides vectors comprising the polynucleotide sequences disclosed herein. In some embodiments, a vector comprises a polynucleotide sequence encoding a fusion protein (i.e. "a fusion protein vector"). In other embodiments, a vector comprises a polynucleotide sequence encoding a substrate protein (i.e. "a substrate protein vector"). In still other embodiments, a vector comprises a polynucleotide sequence encoding a fusion protein and a polynucleotide sequence encoding a substrate protein (i.e. "a fusion protein/substrate protein vector"). Polynucleotide sequences encoding a fusion protein are described in Section I(a). Polynucleotide sequences encoding a substrate protein are described in Section I(b). In each of the above embodiments, the polynucleotide sequence may be operably linked to a promoter. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

In another aspect, the present disclosure provides vectors into which polynucleotide sequences encoding a catalytic domain or a protein of interest may be cloned. Catalytic domains are described in Section I(a)(i). In some embodiments, a vector comprises an origin of replication, a polynucleotide sequence encoding a targeting domain, and a multiple cloning sequence proximal to the polynucleotide sequence encoding a targeting domain (i.e. "a fusion protein cloning vector"). Targeting domains are described in Section I(a)(ii). The multiple cloning sequence can be at the N-terminus or the C-terminus of the polynucleotide encoding the targeting domain. In exemplary embodiments, the polynucleotide encoding the targeting domain may further encode a C-terminal or N-terminal linker. Linkers are described in Section I(a)(iii). In embodiments comprising a linker, the multiple cloning sequence will be proximal to the linker and at the end opposite the targeting domain (e.g. multiple cloning sequence→linker→targeting domain, or targeting domain→linker→multiple cloning sequence).

In another aspect, the present disclosure provides vectors into which polynucleotide sequences encoding a protein of interest may be cloned. Proteins of interest are described in Section I(b)(i). In other embodiments, a vector comprises an origin of replication, a polynucleotide sequence encoding a sequence that interacts with the targeting domain, and a multiple cloning sequence proximal to the polynucleotide sequence encoding a sequence that interacts with the targeting domain (i.e. "a substrate protein cloning vector"). Sequences that interact with a targeting domain are described in Section I(b)(ii). The multiple cloning sequence can be at the N-terminus or the C-terminus of the polynucleotide encoding the sequence that interacts with the targeting domain. In certain embodiments, the polynucleotide encoding the sequence that interacts with the targeting domain may further encode a C-terminal or N-terminal linker. Linkers are described in Section I(b)(iii). In embodiments comprising a linker, the multiple cloning sequence will be proximal to the linker and at the end opposite the sequence that interacts with the targeting domain (e.g. multiple cloning sequence→linker→sequence that interacts with the targeting domain, or sequence that interacts with the targeting domain→linker→multiple cloning sequence). In each of the above embodiments, the polynucleotide sequence may be operably linked to a promoter.

Vectors include, but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

A vector may have a high copy number, an intermediate copy number, or a low copy number. Copy number may be utilized to control the expression level of the fusion protein or substrate protein, to create compatibility with multiple vectors, and/or as a means to control the vector's stability. In one embodiment, a high copy number vector may be utilized. A high copy number vector may have at least 31, 35, 40, 45, 50, 55, 60, 65, 70, 75, 80, 85, 90, 95, or 100 copies per host cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Vectors of the present disclosure are typically used for protein expression. As is well known in the art, such vectors may possess a wide array of replication origins, multiple cloning sequences, promoters, ribosomal binding sites/ribosome entry sites, translation initiation sites, transcription terminators, etc. Vectors may also contain one or more polynucleotides sequences encoding for selectable markers, reporters, and peptide tags.

Polynucleotide sequences of the disclosure may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences and vectors of the invention. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Polynucleotide sequences of the disclosure may be integrated into a chromosome of the host cell upon introduction of a vector into the host cell. Integration may be random or targeted to a particular sequence or location of a chromosome. In general, the general environment at the site of integration may affect whether the integrated polynucleotide is expressed, as well as its level of expression.

In some embodiments, integration may be achieved with a mobile element. The mobile element may be a transposon or a retroelement. A variety of transposons are suitable for use. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration may also be mediated by a virus. Viruses that integrate nucleic acids into a chromosome include bacteriophages, adeno-associated viruses and retroviruses. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. A variety of retroviruses are suitable for use. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

(i) Replication Origin

As used herein, the terms "replication origin" and "origin of replication" may be used interchangeably, or abbreviated as "ori." Selection of a replication origin may be influenced by the desired the intended host cell and the number of vector copies per cell (i.e. copy number). The copy number typically achieved with replication origins known in the art is well characterized. The need for compatibility with one or more other vectors may also influence the selection of a suitable origin of replication.

In some embodiments, a vector comprises at least one bacterial origin of replication. Non-limiting examples of suitable bacterial replication origins include an origin of replication of pMB1 (i.e. "a pMB1 ori"), a pColE1 ori, a pR6K ori, a p15A ori, a pSC101 ori, a pUC ori, a pBF322 ori, a pACYC ori, a pGEX ori, and any derivatives thereof. The copy number typically achieved with each of the above replication origins is known in the art. In other embodiments, a vector comprises at least one phage origin of replication. Non-limiting examples of suitable phage replication origins include a F1 ori. In other embodiments, a vector comprises at least one yeast origin of replication. Non-limiting examples of suitable yeast replication origins include 2-micron origin of replication ori and an ARS (autonomously replicating sequence.

(ii) Promoters, Ribosomal Binding Sites/Ribosome Entry Sites, Translation Initiation Sites, Transcription Terminators, Expression vectors typically contain one or more of the following elements-promoters, ribosomal binding sites/ribosome entry sites, translation initiation sites, and transcription terminators. Selection of suitable promoters, ribosomal binding sites/ribosome entry sites, translation initiation sites, transcription terminators is guided, in part, by the type of host cell. A skilled artisan will appreciate, for example, that eukaryotic and prokaryotic cells have different transcriptional and translational machinery and will select the required elements appropriate for each host cell as is known in the art.

Choice of a suitable promoter may also be influenced by a desire to obtain high, intermediate or low levels of expression, and/or regulated expression. The term "promoter", as used herein, may mean a synthetic or naturally-derived molecule that is capable of conferring, activating or enhancing expression of a nucleic acid. A promoter may comprise one or more specific transcriptional regulatory sequences to further enhance expression and/or to alter the spatial expression and/or temporal expression of a nucleic acid. A promoter may be constitutive, inducible/repressible or cell type specific. For example, in embodiments where the catalytic domain of a fusion protein is constitutively active (e.g. a constitutively active kinase domain), it may be preferred to use a promoter that provides low expression and/or regulated expression to limit toxicity. Regulated expression of a fusion protein with a constitutively active catalytic domain may also reduce substrate protein misfolding.

In certain embodiments, the promoter may be constitutive. Non-limiting examples of constitutive promoters for mammalian cells include CMV, UBC, EF1α, SV40, PGK, CAG, CBA/CAGGS/ACTB, CBh, MeCP2, U6 and H1 promoters. Non-limiting examples of constitutive promoters for insect cells include COPIA, and ACT5C. Non-limiting examples of constitutive promoters for yeast include ADH1, CYC1, TEF1, TEF2, GPD (also known as TDH3 in literature), PDC1, FBA1, PGK1, PGI1, TDH2, PYK1, ENO2, GPM1, TPI1, HXT7, GAP, TEF1, PGK1, GCW14, G1 and G6 promoters. Non-limiting examples of constitutive promoters for bacteria include T7 and Sp6.

In other embodiments, the promoter may be a regulated promoter (e.g. inducible or repressible). Non-limiting examples of regulated promoters for mammalian cells included tetracycline, heat shock, steroid hormone, heavy metal, phorbol ester, adenovirus E1A element, interferon, and serum inducible promoters. Non-limiting examples of regulated promoters for yeast include GAL1, GAL10, MET25, CUP1 and yTHC (yeast Tet-promoter Hughs Collection) promoters. Non-limiting examples of regulated promoters for fungi include AOX1, DAS, FLD, ICL1, PHO89, THI11, ADH1, ENO1, and GUT1 promoters. Non-limiting examples of regulated promoters for bacteria include tetracycline, tryptophan, lactose, arabinose, maltose, rhamnose, and xylose promoters.

The nucleic acid sequences of the promoters detailed herein are known in the art.

(iii) Cleavage Site

A vector may comprise a protease cleavage site. Non-limiting examples of protease cleavage sites include a tomato etch virus (TEV) protease cleavage site, a thrombin cleavage site, a PreScisison cleavage site, or variants thereof. The amino acid sequences of these protease cleavage sites are known in art, as are additional protease cleavage sites suitable for, and commonly used in, vectors.

(d) Host Cell

In another aspect, the present disclosure provides a host cell comprising a vector of Section I(c). Host cells according to the present disclosure are cells are maintained in vitro in substantially pure cultures (i.e. isolated cells). A host cell comprising a vector of Section I(c) may be used for protein expression and, optionally, purification. Methods for expressing and, optionally, purifying an expressed protein from a host are standard in the art. In some embodiments, a host cell comprises a fusion protein vector. In other embodiments, a host cell comprises a substrate protein vector. In still other embodiments, a host cell comprises a fusion protein/substrate protein vector. In yet other embodiments, a host cell comprises a fusion protein vector and a substrate protein vector. In embodiments where a host cell comprises a fusion protein vector and a substrate protein vector, certain elements of the vectors must be complimentary. For example, compatible replication origins are required and each vector must have distinct selectable markers (e.g. two different antibiotic resistance genes).

In certain embodiments, a host cell comprises a fusion protein vector and a substrate protein vector, the fusion protein vector comprising a polynucleotide sequence encoding a fusion protein that is operably linked to a constitutive promoter, and the substrate protein vector comprising a polynucleotide sequence encoding a substrate protein that is operably linked to the same or a different constitutive promoter. In other embodiments, the fusion protein comprises a kinase catalytic domain that is optionally constitutively active, and substrate protein comprises a sequence that interacts with a targeting domain. In exemplary embodiments, the fusion protein comprises a kinase catalytic domain that is optionally constitutively active, and substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In various embodiments, the polynucleotide sequence encoding the fusion protein and the polynucleotide sequence encoding the substrate protein may each further encode a signal peptide, at least one N-terminal peptide tag, at least one C-terminal peptide tag, at least one protease cleavage site, and any combination thereof.

In certain embodiments, a host cell comprises a fusion protein vector and a substrate protein vector, the fusion protein vector comprising a polynucleotide sequence encoding a fusion protein that is operably linked to a constitutive promoter, and the substrate protein vector comprising a polynucleotide sequence encoding a substrate protein that is operably linked to a regulated promoter. In other embodiments, the fusion protein comprises a kinase catalytic domain that is optionally constitutively active, and substrate protein comprises a sequence that interacts with a targeting domain. In exemplary embodiments, the fusion protein comprises a kinase catalytic domain that is optionally constitutively active, and substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In various embodiments, the polynucleotide sequence encoding the fusion protein and the polynucleotide sequence encoding the substrate protein may each further encode a signal peptide, at least one N-terminal peptide tag, at least one C-terminal peptide tag, at least one protease cleavage site, and any combination thereof.

In certain embodiments, a host cell comprises a fusion protein vector and a substrate protein vector, the fusion protein vector comprising a polynucleotide sequence encoding a fusion protein that is operably linked to a regulated promoter, and the substrate protein vector comprising a polynucleotide sequence encoding a substrate protein that is operably linked to a constitutive promoter. In other embodiments, the fusion protein comprises a kinase catalytic domain that is optionally constitutively active, and substrate protein comprises a sequence that interacts with a targeting domain. In exemplary embodiments, the fusion protein comprises a kinase catalytic domain that is optionally constitutively active, and substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In various embodiments, the polynucleotide sequence encoding the fusion protein and the polynucleotide sequence encoding the substrate protein may each further encode a signal peptide, at least one N-terminal peptide tag, at least one C-terminal peptide tag, at least one protease cleavage site, and any combination thereof.

In certain embodiments, a host cell comprises a fusion protein vector and a substrate protein vector, the fusion protein vector comprising a polynucleotide sequence encoding a fusion protein that is operably linked to a first regulated promoter, and the substrate protein vector comprising a polynucleotide sequence encoding a substrate protein that is operably linked to a second regulated promoter. In other embodiments, the fusion protein comprises a kinase catalytic domain that is optionally constitutively active, and substrate protein comprises a sequence that is capable of interacting with a targeting domain. In exemplary embodiments, the fusion protein comprises a kinase catalytic domain that is optionally constitutively active, and substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In various embodiments, the polynucleotide sequence encoding the fusion protein and the polynucleotide sequence encoding the substrate protein may each further encode a signal peptide, at least one N-terminal peptide tag, at least one C-terminal peptide tag, at least one protease cleavage site, and any combination thereof.

In each of the above embodiments, the cell may be a prokaryotic cell or a eukaryotic cell. Appropriate cells include, but are not limited to, bacterial, archaeal, yeast, plant, insect, and mammalian cells. Using methods well known in art, vectors disclosed in Section I(c) can be introduced into host cells by transformation, transfection, transduction or conjugation depending upon the type of host cell and vector. Suitable methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. A vector that is to be introduced to a host cell may be linear or circular, may be single-stranded or double-stranded, and may be DNA, RNA, or any modification or combination thereof.

In some embodiments, a host cell is a prokaryote. Non-limiting examples of suitable prokaryotes include *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., Kingella sp., *Pasteurella* sp., *Flavobacterium* sp. *Xanthomonas* sp., *Burkholderia* sp., *Aeromonas* sp., *Plesiomonas* sp., *Legionella* sp., alpha-proteobaeteria such as *Wolbachia* sp., cyanobacteria, spirochaetes, green sulfur and green non-sulfur bacteria, Gram-negative cocci, Gram negative bacilli, Enterobacteriaceae-glucose-fermenting gram-negative bacilli, Gram negative bacilli-non-glucose fermenters, Gram negative bacilli-glucose fermenting, oxidase positive. Particularly useful bacterial host cells for protein expression include Gram negative bacteria, such as *Escherichia coli, Pseudomonas fluorescens, Pseudomonas haloplanctis, Pseudomonas putida* AC10, *Pseudomonas pseudoflava, Bartonella henselae, Pseudomonas syringae, Caulobacter crescentus, Zymomonas mobilis, Rhizobium meliloti, Myxococcus xanthus* and Gram positive bacteria such as *Bacillus subtilis, Corynebacterium, Streptococcus cremoris, Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development bio-therapeutics and vaccines).

In some embodiments, a host cell is a yeast or fungal cell. Particularly useful yeast and fungi for protein expression include *Aspergillis oryzae, Aspergillis niger, Trichoderma reesei, Aspergillus nidulans, Fusarium graminearum*. Particularly useful yeast host cells for protein expression include *Candida albicans, Candida maltose, Hansenula polymorpha, Kluyveromyces fragilis, Kluyveromyces lactis, Pichia guillerimondii, Pichia pastoris, Saccharomyces cerevisiae, Schizosaccharomyces pombe,* and *Yarrowia lipolytica.*

In some embodiments, a host cell is a mammalian cell. Particularly useful mammalian cells for protein expression include Chinese hamster ovary (CHO) cells, HeLa cells, baby hamster kidney (BHK) cells, monkey kidney cells (COS), human hepatocellular carcinoma cells (e.g. Hep G2), human embryonic kidney cells, *Bos primigenius,* and *Mus musculus*. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

(e) Isolated Proteins

In another aspect, the present disclosure provides an isolated polypeptide encoded by a polynucleotide sequence disclosed in Section I(a) or Section I(b). As used herein, the term "isolated polypeptide" refers to a polypeptide that has been partially or completely purified from the cell from which it was produced. Isolated polypeptides of the disclosure may be produced using molecular biological methods known to in the art. Generally speaking, a polynucleotide sequence encoding the polypeptide is inserted into a vector that is able to express the polypeptide when introduced into an appropriate host cell. Appropriate vectors and host cells are described in Section I(c) and Section I(d), respectively. Once expressed, polypeptides may be obtained from cells using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the disclosure may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises affinity tag or purification tag, as described herein.

(f) Kits

Another aspect of the present invention encompasses kits comprising polynucleotides, vectors, and/or host cells described in this Section.

In some embodiments, a kit comprises a polynucleotide encoding a fusion protein, a fusion protein vector, a fusion protein cloning vector, an isolated fusion protein, a host cell comprising a fusion protein vector, or any combination thereof. In each embodiment, the kit may further comprise a host cell.

In other embodiments, a kit comprises a polynucleotide encoding a substrate protein, a substrate protein vector, a substrate protein cloning vector, or any combination thereof. In each embodiment, the kit may further comprise a host cell.

In some embodiments, a kit comprises (a) a polynucleotide encoding a fusion protein, a fusion protein vector, a fusion protein cloning vector, or an isolated fusion protein, and (b) a polynucleotide encoding a substrate protein, a substrate protein vector, a substrate protein cloning vector, or any combination thereof. In certain embodiments, the kit may further comprise a host cell.

In some embodiments, a kit comprises (a) a fusion protein vector or a fusion protein cloning vector, and (b) a substrate protein vector or a substrate protein cloning vector, the fusion protein vector/fusion protein cloning vector comprising a constitutive promoter for constitutive expression of a fusion protein, and the substrate protein vector/substrate protein cloning vector comprising the same or a different constitutive promoter for constitutive expression of a substrate protein. In certain embodiments, the kit may further comprise a host cell.

In some embodiments, a kit comprises (a) a fusion protein vector or a fusion protein cloning vector, and (b) a substrate protein vector or a substrate protein cloning vector, the fusion protein vector/fusion protein cloning vector comprising a constitutive promoter for constitutive expression of a fusion protein, and the substrate protein vector/substrate protein cloning vector comprising a regulated promoter for regulated expression of a substrate protein. In certain embodiments, the kit may further comprise a host cell.

In some embodiments, a kit comprises (a) a fusion protein vector or a fusion protein cloning vector, and (b) a substrate protein vector or a substrate protein cloning vector, the fusion protein vector/fusion protein cloning vector comprising a regulated promoter for regulated expression of a fusion protein, and the substrate protein vector/substrate protein cloning vector comprising a constitutive promoter for constitutive expression of a substrate protein. In certain embodiments, the kit may further comprise a host cell.

In some embodiments, a kit comprises (a) a fusion protein vector or a fusion protein cloning vector, and (b) a substrate protein vector or a substrate protein cloning vector, the fusion protein vector/fusion protein cloning vector comprising a first regulated promoter for regulated expression of a fusion protein, and the substrate protein vector/substrate protein cloning vector comprising a second regulated promoter for regulated expression of a substrate protein. In certain embodiments, the kit may further comprise a host cell.

In each of the above embodiments, the fusion protein may comprise a kinase catalytic domain that is optionally constitutively active, and the substrate protein may comprise a sequence that interacts with a targeting domain. In each of the above embodiments, the fusion protein may comprise a kinase catalytic domain that is optionally constitutively active, and the substrate protein may comprise a polyproline sequence that is capable of binding to an SH3 domain and has at least 80% sequence identity to a sequence selected from the group consisting of SEQ ID NO: 2, SEQ ID NO: 3, and SEQ ID NO: 4. In various embodiments, the polynucleotide sequence encoding the fusion protein and the polynucleotide sequence encoding the substrate protein may each further encode a signal peptide, at least one N-terminal peptide tag, at least one C-terminal peptide tag, at least one protease cleavage site, and any combination thereof.

In each of the above embodiments, the kit may further comprise reaction buffers, wash buffers, nucleoside triphosphate, and/or means for purifying the fusion protein and/or the substrate protein.

(g) Methods of Use

In another aspect, the present disclosure provides a method to produce soluble, folded, and post-translationally modified recombinant proteins. The method comprises the use of a fusion protein and a substrate protein, wherein the fusion protein comprises a catalytic domain of an enzyme involved in post-translational protein modification and a targeting domain, and the substrate protein comprises a sequence that interacts with the targeting domain and a polypeptide of interest that is a substrate of the fusion protein's catalytic domain. Specifically, a polyproline sequence of the substrate protein is capable of binding to the SH3 domain of the fusion protein. In this manner, the sequence that interacts with the targeting domain targets the substrate protein to the fusion protein and promotes substrate-enzyme interactions, resulting in a substrate protein that contains a greater number of modifications than a substrate protein modified with a catalytic domain that is not coupled to a targeting domain. In some embodiments, about 10%, about 20%, about 30%, or about 50% more modification is achieved using the methods of this disclosure. In some embodiments, about 50%, about 60%, about 70%, about 80%, or about 90% more modification is achieved using the methods of this disclosure. In other embodiments, about 2-fold, about 3-fold, about 4-fold, about 5-fold, more modification is achieved using the methods of this disclosure. In other embodiments, about 6-fold, about 7-fold, about 8-fold, about 9-fold, more modification is achieved using the methods of this disclosure. In other embodiments, at least about 10-fold, at least about 50-fold, at least about 100-fold, at least about 200-fold more modification is achieved using the methods of this disclosure. Control over the degree of substrate modification by the catalytic domain is achieved by using sequences that interact with a targeting domain with different affinity for a given targeting domain (e.g. polyproline sequences with high, medium, or low affinity for any given SH3 domain). The specificity of the catalytic domain for the active site of the protein of interest will also contribute a degree of control.

In some embodiments, a method to produce post-translationally modified recombinant proteins comprises co-expressing a polynucleotide encoding a fusion protein of Section I(a) and a polynucleotide encoding a substrate protein of Section I(b) in a host cell. The polynucleotide encoding the fusion protein and the polynucleotide encoding the substrate protein can be expressed from the same or different vector, or can be chromosomally integrated, as described in Section I(c). The host cell can be a mammalian cell, a yeast cell, a plant cell, an archaeal cell, or a bacterial cell, as described in Section I(d). In certain embodiments, the host cell is a bacterial cell comprising a fusion protein vector and a substrate protein vector; the fusion protein vector comprises a polynucleotide sequence that encodes a fusion protein and that is operably linked to a promoter; and the substrate protein vector comprises a polynucleotide sequence that encodes a substrate protein and that is operably linked to the same or a different promoter as the fusion protein vector. In certain embodiments, the polynucleotide encoding the fusion protein is operably linked to a first regulated promoter; the polynucleotide encoding the substrate protein is operably linked to a second regulated promoter; and the substrate protein comprises a sequence that interacts with a targeting domain. In preferred embodiments, the polynucleotide encoding the fusion protein is operably linked to a first regulated promoter; the polynucleotide encoding the substrate protein is operably linked to a second regulated promoter; and the substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In exemplary embodiments, the fusion protein comprises a kinase catalytic domain that is optionally constitutively active, and the fusion protein and/or the substrate protein each comprise at least one of a signal peptide, a N-terminal peptide tag, a C-terminal peptide tag, a protease cleavage site, or any combination thereof.

In other embodiments, a method to produce post-translationally modified recombinant protein comprises (a) providing a cell lysate of a host cell expressing a polynucleotide encoding a fusion protein, as described in Section I(d), and (b) contacting the cell lysate with an isolated substrate protein of Section I(e) under effective conditions for a period of time sufficient to allow for modification of the substrate protein to occur. In other embodiments, a method to produce post-translationally modified recombinant protein comprises (a) providing a cell lysate of a host cell expressing a polynucleotide encoding a fusion protein, as described in Section I(d), and (b) contacting the cell lysate with a cell lysate of a host cell expressing a polynucleotide encoding a substrate protein, as described in Section I(d) under effective conditions for a period of time sufficient to allow for modification of the substrate protein to occur. In other embodiments, a method to produce post-translationally modified recombinant protein comprises (a) providing an isolated fusion protein, as described in Section I(e), and (b) contacting the isolated fusion protein with an isolated substrate protein of Section I(e) under effective conditions for a period of time sufficient to allow for modification of the substrate protein to occur. "Contacting" generally involves combining the reactants in solution and incubating the resultant product for a period of time long enough for the substrate protein and the fusion protein to interact (at least 30 seconds at about 4° C. to about 45° C., preferably about 20° C. to about 37° C.). In certain embodiments, the isolated substrate protein may be immobilized on a solid substrate (e.g. a bead, a plate, a well, a slide, etc.). Reviews of the range of solution-phase and solid-supported formats available for such assays can be used to optimize assay design as needed. For example, for kinase assays, see Wu et al, *Peptide Science* 2010, 94(4): 475-486. In certain embodiments, the host cell is a bacterial cell lysate, the bacterial cell comprised a fusion protein vector comprising a polynucleotide sequence encoding a fusion protein that is operably linked to a promoter. In other embodiments, the polynucleotide encoding the fusion protein is operably linked to a regulated promoter, and the substrate protein comprises a sequence that interacts with a targeting domain and has at least 80% sequence identity to a sequence selected from the group consisting of SEQ ID NO: 2, SEQ ID NO: 3, and SEQ ID NO: 4. In preferred embodiments, the polynucleotide encoding the fusion protein is operably linked to a regulated promoter, and the substrate protein comprises a polyproline sequence that is capable of binding to an SH3 domain and has at least 80% sequence identity to a sequence selected from the group consisting of SEQ ID NO: 2, SEQ ID NO: 3, and SEQ ID NO: 4. In exemplary embodiments, (a) the fusion protein comprises a kinase catalytic domain that is optionally constitutively active, and at least one of a signal peptide, a N-terminal peptide tag, a C-terminal peptide tag, a protease cleavage site, or any combination thereof, and (b) the substrate protein comprises at least one of a N-terminal peptide tag, a C-terminal peptide tag, a protease cleavage site, or any combination thereof.

In each of the above embodiments, a substrate protein may be partially or completely purified, and/or the modification may be detected and/or quantified by any method known in the art. For example, many forms of post-translational modifications can be detected with antibodies or other epitope-binding agents using methods such as Western blot or ELISA. Alternatively, mass spectrometry is effective method to detect and quantify the mass shift in the peptide molecular weight after post-translational modification.

In another aspect, the present invention provides a method for producing a plurality of substrate proteins with varying amounts of post-translational modifications. In some embodiments the method comprises (a) constructing a library of two or more substrate protein vectors; (b) constructing a library of two or more fusion protein vectors; and (c) co-expressing various combinations of a vector of step (a) and a vector of step (b) in a plurality of host cells. In other embodiments the method comprises (a) constructing a library of two or more substrate protein vectors; (b) constructing a single fusion protein vector; and (c) co-expressing various combinations of a vector of step (a) and the vector of step (b) in a plurality of host cells. In other embodiments the method comprises (a) constructing a single substrate protein vector; (b) constructing a library of two or more fusion protein vectors; and (c) co-expressing various combinations of the vector of step (a) and a vector of step (b) in a plurality of host cells. Each of the above embodiments may further comprise (d) optionally purifying (partially or completely) substrate proteins from the host cells of step (c), and/or optionally detecting, quantifying or otherwise characterizing the amount and/or location(s) of the modifications on the substrate proteins from each host cell. Each vector in the library of substrate protein vectors comprises a polynucleotide sequence encoding a substrate protein operably linked to a promoter, and each substrate protein contains the same protein of interest. However, the promoter and/or the sequence that interacts with a targeting domain can and will vary between substrate vectors. Similarly, each vector in the library of fusion protein vectors comprises a polynucleotide sequence encoding a fusion protein operably linked to a promoter, though the promoter, the targeting domain and/or the catalytic domain can and will vary, provided the various catalytic domains all have the same enzymatic activity (e.g. all are kinases, even more preferably all are the same type of kinase (e.g. serine/threonine kinase, etc.). In exemplary embodiments, the fusion protein comprises a kinase catalytic domain that is optionally constitutively active and at least one of a signal peptide, a N-terminal peptide tag, a C-terminal peptide tag, a protease cleavage site, or any combination thereof.

The following examples are included to demonstrate preferred embodiments of the disclosure. It should be appreciated by those of skill in the art that the techniques disclosed in the examples that follow represent techniques discovered by the inventors to function well in the practice of the invention. Those of skill in the art should, however, in light of the present disclosure, appreciate that changes may be made in the specific embodiments that are disclosed and still obtain a like or similar result without departing from the spirit and scope of the invention. Therefore, all matter set forth or shown in the accompanying drawings is to be interpreted as illustrative and not in a limiting sense.

EXAMPLES

The following examples illustrate various iterations of the invention.

Example 1

To generate a substrate protein cloning vector, the pGEX backbone was modified to contain a polynucleotide sequence that is operably linked to the tac promoter/lac operator and encodes (from 5' to 3'), a SUMO tag, a polyproline sequence, a PreScission cleavage sequence, a multiple cloning site, a thrombin cleavage sequence, and two affinity/purification tags. In total, three different polyproline sequences were used (SEQ ID NO: 2, SEQ ID NO: 3 and SEQ ID NO: 4) to generate three substrate protein cloning vectors. The PreScission cleavage sequence, for use in GST-based elution, ensures substrate proteins made from different polyproline sequence-containing constructs will be identical following purification. In addition, a second set of substrate protein cloning vectors were constructed that lack the SUMO domain encoded by smt3 (not shown). Inclusion of the SUMO domain did not interfere with GST binding of the substrate protein or protein elution.

Example 2

A collection of substrate protein vectors comprising a panel of SH2 domains can be created using the substrate protein cloning vectors of Example 1 and cloning a polynucleotide sequence encoding an SH2 domain into the multiple cloning site. A map of the resulting vector is depicted in FIG. 3. The set of SH2 domains used in these experiments includes a BTK SH2 domain, an ABL SH2 domain, a SRC SH2 domain, a SHC SH2 domain, a PTPN11 N-terminal SH2 domain, a PTPN11-C-terminal SH2 domain, a CRK SH2 domain and a LYN SH2 domain into A bacterial cell can be transfected with the substrate vector, and expression of the polynucleotide encoding the substrate/polyproline sequence induced by the addition of either lactose or IPTG to the culture medium. Total protein can be measured on a spectrophotometer and purity determined using Coomassie incorporation following SDS-PAGE separation. Coomassie incorporation is adjusted based on protein size.

Following purification by anti-GST resin and elution by PreScission cleavage of a protein produced in $E.$ $coli$ DE3 gold cells with IPTG induction overnight at 18° C., we typically achieve around 1 mg/mL and 80% purity. Secondary purification can be performed by $Ni_2$ purification or fast protein liquid chromatography (FPLC), as needed.

Example 3

In order to co-express a fusion protein vector with a substrate vector in a host cell, certain elements of the fusion protein vector must be complimentary to the substrate vector. Specifically, a second antibiotic resistance and a compatible replication of origin are required. Additionally, independent induction methods for the fusion protein and the substrate protein are ideal, so that: 1) both the substrate protein and the fusion protein can be optimally controlled according to their individual requirements, and 2) delayed induction of the fusion protein can be performed should its constitutive expression result in modification of the substrate protein during translation of the substrate protein, thereby preventing its proper folding.

To these ends, a fusion protein cloning vector was constructed. Specifically, a pBAD vector backbone was modified by replacing the ampicillin resistance gene with a kanamycin resistance gene, and replacing the ColE1 origin of replication with the p15A origin of replication. The fusion protein cloning vector has additionally been engineered to contain a polynucleotide sequence encoding (from 5' to 3') a SUMO tag, an ABL SH3 domain, a flexible linker, a multiple cloning site, a TEV protease cleavage site, and two affinity/purification tags. The flexible linker consists of 11 repeats of lysine and aspartic acid.

Example 4

To generate a fusion protein vector comprising a kinase catalytic domain, polynucleotide sequences encoding constitutively active kinases were cloned into the fusion protein cloning vector of Example 3. A map of the resulting vector is depicted in FIG. 4. Specifically, constitutively active variants of the FAK, SRC, ABL, EGFR, and BTK kinases were identified based on designs of commercially available recombinant kinases and literature curation of mutants known to be constitutively active. For example, a constitutively active variant of FAK was made by deleting the FERM domain, and a constitutively active variant of BTK was made by deleting the PH and SH3 domain. Polynucleotide sequences encoding the constitutively active kinases were then individually cloned into the multiple cloning site of the fusion protein cloning vector of Example 3 to produce three fusion protein vectors with different catalytic domains. Fusion protein vectors comprising constitutively active variants of JAK, MET, and EphA4 kinases will be generated in a similar manner.

Example 5

*E. coli* cells were transfected with a fusion protein vector encoding a constitutively-active ABL kinase fusion protein (Example 4), a substrate protein vector encoding a substrate protein comprising an ABL SH2 domain and a polyproline sequence (Example 2, "targeted substrate"), or a vector encoding an ABL SH2 domain (no polyproline sequence, "untargeted substrate"). Expression of the proteins was induced for four hours at 37° C., and crude cell lysate was prepared. Targeted substrate and untargeted substrate was purified from the respective cell lysate using an anti-GST resin. During purification, resin was incubated with the fusion protein crude cell lysate either for one hour at 30° C. or overnight at 4° C. in a magnesium and ATP rich buffer. Tyrosine phosphorylation of the substrate protein was evaluated by Western blot using an anti-phosphotyrosine antibody from supernatant that was collected prior to purification (SN) and eluate (E) that was collected after the kinase reaction and washes. As shown in FIG. 5, the leading edge of E in the untargeted sample is slightly green, indicating limited phosphorylation of the substrate protein by the untargeted kinase. In contrast, the substrate protein was significantly phosphorylated by the targeted kinase (i.e. the fusion protein). These data shown that the reaction affinity is increased by targeting the kinase to its substrate.

Example 6

Successful phosphorylation of a substrate will result in specific phosphorylation sites on the substrate with varying degrees of phosphorylation in the population. The process outlined in FIG. 6 illustrates one approach to measure this phosphorylation profile as a function of kit components (e.g. fusion proteins and substrate proteins). The process starts with inexpensive screens that have low resolution but high capacity to first identify catalytic domain specificities capable of creating phosphorylation on the substrate. In this example, a medium affinity interaction is used in the first screen (e.g. polyproline sequence=SEQ ID NO: 4) to identify whether a given kinase can phosphorylate a substrate (e.g. an SH2 domain) because it will allow for some degree of kinase-substrate targeting but also sufficient enzyme turnover, which may not occur with a high affinity interaction. PAGE separation and western detection will be used in a large screen of binding affinities and kinases to identify a subset of roughly five protein products to be analyzed by ion-exchange chromatography. Ion exchange chromatography will sort proteins according to their total charge, and therefore number of phosphorylation sites per protein. Selected fractions will then be analyzed for site-specific identification and quantification by quantitative mass spectrometry (detailed below). The proposed process trades off throughput and expense with resolution, but will ideally result in the high-resolution identification of the most diverse set of phosphoprotein patterns.

Tandem mass spectrometry will be used to profile the specific phosphorylation sites produced. Isobaric tags (TMT-6 or TMT-10) will be used to label purified domains, which will allow for quantitative comparison of differences in phosphorylation achieved on a particular site as a function of kit components. A phosphopeptide library will be synthesized containing heavy-labeled arginine or lysine based on the tryptic fragments of phosphorylation sites in the SH2 domain. The library will be spiked into each protein fraction, prior to isobaric labeling. The spiked-in peptide library will ensure the ability to identify a site of phosphorylation if it exists within the sample and provide an internal reference standard for quantification as performed in Curran et al. Multiple runs may be combined as necessary, using a common sample for normalization, in order to test other possible kinase library components. The outcome of the quantitative mass spectrometry experiments will be the identification of the library conditions that maximally produce a specific pattern of phosphorylation.

What is claimed is:

1. A method of phosphorylating a substrate protein of interest comprising contacting a fusion protein and a substrate protein for a period of time sufficient to allow for phosphorylation of the substrate protein by the fusion protein to occur, wherein (a) the fusion protein comprises a kinase catalytic domain, a targeting domain and a first linker, wherein the targeting domain is a SH3 (src Homology 3) domain and the kinase catalytic domain and the targeting domain are joined by the first linker; and (b) the substrate protein comprises a polypeptide of interest, a sequence that interacts with the targeting domain of the fusion protein, a protease cleavage site, and an optional second linker; wherein (i) the sequence that interacts with the targeting domain is a polyproline sequence selected from the group consisting of: SEQ ID NO: 2, SEQ ID NO: 3, SEQ ID NO: 4, a variant with at least 80% sequence identity to SEQ ID NO: 2, 3 or 4 that is capable of binding to an SH3 domain and a sequence of about 5 to about 20 amino acids in length and contains the sequence proline-Xaa-Xaa-proline, wherein Xaa is any amino acid; (ii) the protease cleavage site is between the polypeptide of interest and the second linker when the second linker is present, and between the polypeptide of interest and the sequence that interacts with the targeting domain when the second linker is not present; and (iii) wherein the first linker contains repeats of two, oppositely-charged, amino acids, and the first linker is about 10 to about 30 amino acids in length and/or the second linker contains repeats of two, oppositely-charged, amino acids, and the second linker is about 10 to about 30 amino acids in length.

2. The method of claim 1, wherein the oppositely-charged amino acids of the first linker and/or the second linker are lysine and glutamic acid.

3. The method of claim 1, wherein the fusion protein and/or the substrate protein further comprises at least one N-terminal or C-terminal peptide tag selected from the group consisting of an affinity tag, a purification tag, a solubility tag, and a stability tag.

4. The method of claim 3, wherein the fusion protein and/or the substrate protein further comprises a second protease cleavage site, wherein the second protease cleavage site is positioned relative to the peptide tag such that cleavage at the second protease site results in removal of the protein tag from the protein.

5. The method of claim 1, wherein the fusion protein and/or the substrate protein comprises (a) at least one affinity tag, purification tag, or tag that is a combination thereof; and (b) at least one solubility tag or stability tag.

6. The method of claim 5, wherein the fusion protein and/or the substrate protein comprises (a) at the C-terminus, at least one affinity tag, purification tag, or tag that is a combination thereof, and at the N-terminus, at least one stability tag or solubility tag; or (b) at the N-terminus, at least one affinity tag, purification tag, or tag that is a combination thereof, and at the C-terminus, at least one stability tag or solubility tag.

7. The method of claim 5, wherein the fusion protein further comprises a protease cleavage site, and the protease cleavage site is positioned relative to (a) the at least one affinity tag, purification tag, or tag that is a combination thereof, and/or (b) the at least one solubility tag or stability tag such that cleavage at the protease site results in removal of the tag from the protein.

8. The method of claim 1, wherein the sequence that interacts with the targeting domain is on the N-terminal side of the protease cleavage site.

9. The method of claim 1, wherein the sequence that interacts with the targeting domain is on the C-terminal side of the protease cleavage site.

10. The method of claim 1, wherein the method further comprises purifying the phosphorylated substrate protein.

* * * * *